(12) United States Patent
    Kanemaru

(10) Patent No.: US 10,864,685 B2
(45) Date of Patent: Dec. 15, 2020

(54) TUBE JOINING DEVICE

(71) Applicant: TERUMO KABUSHIKI KAISHA, Tokyo (JP)

(72) Inventor: Keisuke Kanemaru, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/496,389

(22) PCT Filed: Mar. 23, 2018

(86) PCT No.: PCT/JP2018/011685
    § 371 (c)(1),
    (2) Date: Sep. 20, 2019

(87) PCT Pub. No.: WO2018/174245
    PCT Pub. Date: Sep. 27, 2018

(65) Prior Publication Data
    US 2020/0223154 A1    Jul. 16, 2020

(30) Foreign Application Priority Data

Mar. 24, 2017  (JP) .................................. 2017-059208

(51) Int. Cl.
    *B29C 65/20*      (2006.01)
    *B29C 65/74*      (2006.01)
    *B29C 65/78*      (2006.01)
    *B29C 65/00*      (2006.01)
(52) U.S. Cl.
    CPC .......... *B29C 66/857* (2013.01); *B29C 65/743* (2013.01); *B29C 66/5221* (2013.01); *B29C 66/8221* (2013.01)

(58) Field of Classification Search
    CPC ..... A61M 39/146; A61M 39/18; B29C 65/20; B29C 65/2046; B29C 65/743; B29C 65/7802; B29C 65/7841; B29C 66/0018; B29C 66/1142; B29C 66/5221; B29C 66/71; B29C 66/7373; B29C 66/73921; B29C 66/8221; B29C 66/8227; B29C 66/857; B29C 66/90; B29L 2023/007
    See application file for complete search history.

(56) References Cited

FOREIGN PATENT DOCUMENTS

| JP | 11-178891 A | 7/1999 | |
|----|----|----|----|
| JP | 2010082222 A * | 4/2010 | ......... B29C 66/1142 |
| JP | 2013146354 A * | 8/2013 | ......... B29C 66/5221 |

* cited by examiner

*Primary Examiner* — Michael A Tolin
(74) *Attorney, Agent, or Firm* — Terumo BCT, Inc IP Law Dept

(57) ABSTRACT

Provided is a tube joining device that allows a user to easily and appropriately perform setting of tubes which become a joining target, and is capable of preventing occurrence of a joining failure caused by a setting error of the tubes in advance. A tube joining device 1 includes: a first tube holding portion 41 that is capable of holding a first tube T1; a second tube holding portion 42 that is disposed in adjacent to the first tube holding portion, and is capable of holding a second tube T2 at a position that is parallel to the first tube; and a housing 2 that is provided with a cover member 20 that is closed to cover fusion-joining sites C of the first tube and the second tube. The cover member is slidable along a direction in which the first tube and the second tube are disposed in parallel.

14 Claims, 20 Drawing Sheets

TUBE JOINING DEVICE

TECHNICAL FIELD

The present invention relates to a tube joining device that is used in joining of a tube.

BACKGROUND ART

As a technology of connecting tubes formed from a resin to each other, there has been known a joining method in which ends of the tubes formed from a resin are fused and the fused ends are pressed for pressure-joining. The technology has been widely used in various industrial fields, and as an example thereof, an application to a medical technology such as a peritoneal dialysis method has been attempted.

The peritoneal dialysis method is a method in which a predetermined dialysis fluid is put into a body by using a tube (catheter) that is inserted into the abdominal cavity of a patient, and water or waste matters which are transferred to the dialysis fluid through the peritoneum are removed to the outside of the body. When putting the dialysis fluid into the body, a tube inserted into a patient is liquid-tightly joined to a tube of a bag in which the dialysis fluid is accommodated. In addition, even when discharging the dialysis fluid from the inside of the body, the tube inserted into the patient is liquid-tightly joined to a tube of a liquid discharge bag.

As described above, one tube that becomes a joining target is inserted into the abdominal cavity of the patient. Accordingly, during joining work, it is necessary to pay the closest attention to the work in order for each tube not to be contaminated. In consideration of such circumstances, for example, as described in Patent Literature 1, a tube joining device capable of automatically performing joining in an aseptic condition by fusing two tubes formed from a resin is developed. In the device, fused ends of the two tubes are replaced and joined, and thus there is no concern of bacterium contamination during joining, and it is possible to secure sterilization of the tube, the dialysis fluid in the bag, and the like. In addition, in the device, the two tubes are superimposed in an upper and lower direction (height direction) of the device and are set to a close contact state, and a plate-shaped metal wafer that is heated is moved to approach the tubes to perform fusing.

CITATION LIST

Patent Literature

Patent Literature 1: JP 2013-146354 A

SUMMARY OF INVENTION

Technical Problem

In a case of using the above-described tube joining device, a user such as a patient manually superimposes and sets respective tubes which become a joining target in the device. In addition, after setting the tubes in the tube joining device, the user such as the patient closes a cover member that is provided in the housing, and covers a fusing-joining position of the tubes from the outside. In the tube joining device, the cover member is closed regardless of a state of the tubes which are set, and when a predetermined operation switch is pushed, fusing-joining work is initiated.

The user such as the patient manually superimposes and sets respective tubes which become a joining target in the tube joining device. However, at this time, the tubes have flexibility, and thus the user may fail in handling of the tubes, and may superimpose the tubes in a distorted state or may superimpose the tubes in a three-folded state. When performing fusing-joining work by the device in a state in which the tube is set as described above, the tubes are joined, but a joining failure such as hole occurs at a joining portion.

For example, when the cover member is closed, it is considered that occurrence of the joining failure can be effectively prevented if it is possible to visually confirm a setting position of the tubes up to a time immediately before the cover member is closed. However, in the tube joining device, since a closing operation is performed such that the setting position of the tubes is covered with the cover member, it is difficult to recognize the setting position of the tubes when closing the cover member.

The invention has been made in consideration of such circumstances, and an object thereof is to provide a tube joining device that allows a user to easily and appropriately perform setting of tubes which become a joining target, and is capable of preventing occurrence of a joining failure caused by a setting error in advance.

Solution to Problem

According to an aspect of the invention, there is provided a tube joining device that fuses an end of a first tube and an end of a second tube by a plate-shaped cutting member that is heated, and replaces the fused end of the first tube and the fused end of the second tube and joins the fused ends in an aseptic condition. The tube joining device includes: a first tube holding portion capable of holding anyone tube between the first tube and the second tube, a second tube holding portion that is disposed adjacent to the first tube holding portion and is capable of holding the other tube between the first and second tube at a position parallel to the one tube, and a housing provided with a cover member that is closed to cover a fusing-joining site of the first tube and the second tube. The cover member is slidable in a direction in which the first tube and the second tube are disposed in parallel.

Advantageous Effects of Invention

According to the tube joining device according to the invention, a user can dispose the tubes in parallel by setting the tubes individually in the first and second tube holding portions. In addition, the user can cause the tubes to be pressed against each other to come into close contact with each other by operating the cover member that is provided in the device, and thus it is possible to perform setting work of the tubes in a simple manner. As described above, when using the device, it is not necessary for the user to manually perform work of superimposing the tubes, and thus it is possible to prevent a work error such as setting of the tubes in a distorted state from occurring. In addition, since the cover member is slidable along a direction in which the first tube and the second tube are disposed in parallel, it is possible to visually confirm a setting position of the tubes up to a time immediately before the cover member is closed. Accordingly, it is possible to prevent a joining failure caused by a tube setting error from occurring in advance.

BRIEF DESCRIPTION OF DRAWINGS

FIG. 20A to FIG. 20B are views illustrating tubes after joining, in which FIG. 20A is an enlarged view of the tubes after joining, and FIG. 20B is a view schematically illustrating an installation state of the tubes after joining.

DESCRIPTION OF EMBODIMENTS

Figure 1:
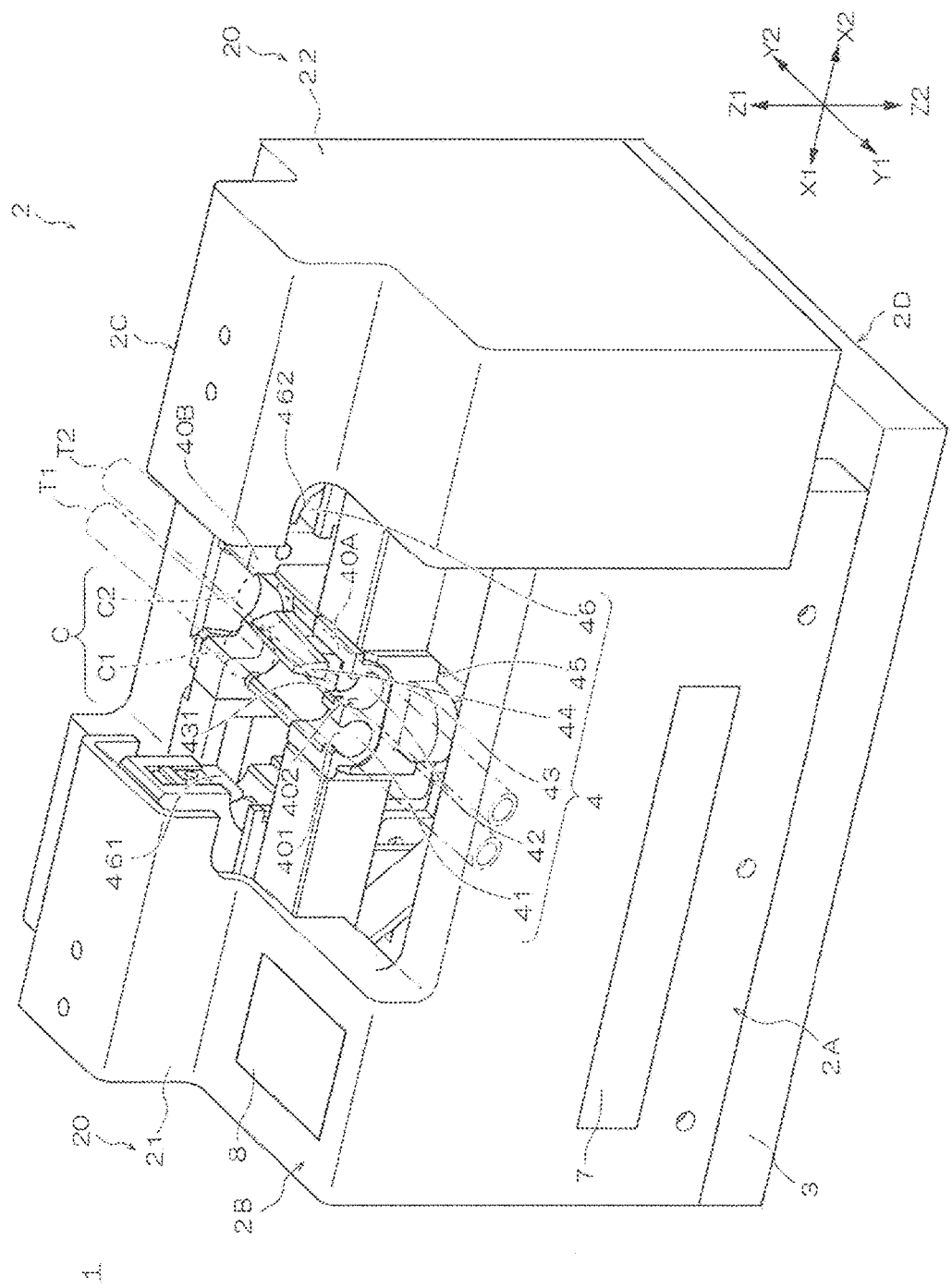
FIG. 1 is a perspective view illustrating a tube joining device according to an embodiment of the invention.

Hereinafter, an embodiment of the invention will be described with reference to the accompanying drawings. Furthermore, dimension ratios in the drawings are exaggerated for convenience of explanation, and may be different from actual ratios.

A tube joining device 1 fuses ends of a plurality of tubes T1 and T2 (hereinafter, referred to as a first tube T1 and a second tube T2), and presses and joins the fused ends in an aseptic condition. In this embodiment, description will be given of the tube joining device with reference to an example that is applied to a medical device that is used in joining of a dialysis fluid tube (the first tube T1, corresponds to one tube) of a peritoneal dialysis fluid bag, and a patient peritoneal catheter side tube (the second tube T2, corresponds to the other tube) that is used when performing peritoneal dialysis (refer to FIG. 18).

As illustrated in FIG. 19A to FIG. 19D and FIG. 20A to FIG. 20B, the tube joining device 1 has a configuration in which an end of the first tube T1 and an end of the second tube T2 are fused by a heated wafer WF (corresponding to a plate-shaped cutting member), and replaces and joins the fused end of the first tube T1 and the fused end of the second tube T2.

Respective configurations of the tube joining device 1 will be described.

For example, a preferred use environment of the tube joining device 1 is an environmental temperature of 10° C. to 40° C. and a relative humidity of 30% to 85%. However, the use environment is not particularly limited as long as the ends of the tubes T1 and T2 can be pressure-welded.

As illustrated in FIG. 1, for example, the tube joining device 1 can be configured to include a housing 2, and a tube holding section 4 in which the tubes T1 and T2 are disposed in parallel and are held.

As illustrated in FIG. 1 to FIG. 5, the housing 2 is constituted by a case including a front surface portion 2A, a top surface portion 2B, a rear surface portion 2C, and a bottom surface portion 2D. As illustrated in the drawings, the case has a substantially rectangular parallelepiped shape that is chamfered.

Figure 6:
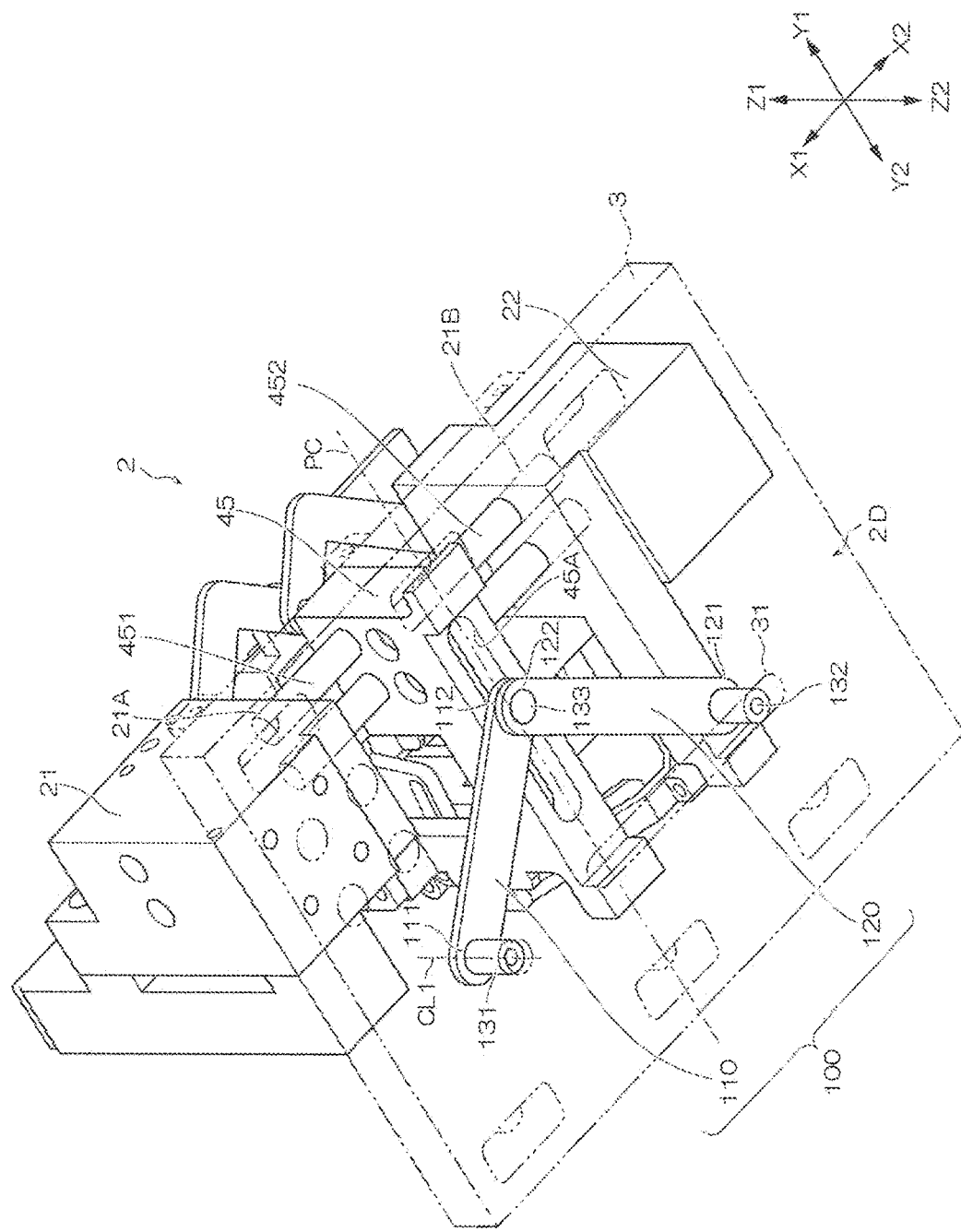
FIG. 6 is a perspective view illustrating a first link mechanism and main portions of the tube joining device in a state in which the cover member is opened.

The housing 2 includes a cover member 20 that is closed to cover fusing-joining sites C of the first tube T1 and the second tube T2, and a base 3 on which the cover member 20 is placed. As illustrated in FIG. 6, in a state in which the cover member 20 is closed, the housing 2 accommodates respective constituent elements of the tube joining device 1 including the tube holding section 4 in a space surrounded by the cover member 20 and the base 3. Although not particularly limited, for example, a hard plastic can be used as a material of the housing 2.

As illustrated in FIG. 1 to FIG. 5, the cover member 20 is configured to be slidable along a direction in which the first tube T1 and the second tube T2 are disposed in parallel. The cover member 20 includes a first pressing member 21 and a second pressing member 22 which can relatively approach each other or can be separated from each other in a sliding direction, and maintain the first tube T1 and the second tube T2 in a pressed state in accordance with the approaching movement. The cover member 20 can be opened or closed by causing the second pressing member 22 to perform approaching movement or separating movement with respect to the first pressing member 21.

In the following description, a direction in which the cover member 20 slides is referred to as "sliding direction", and is indicated by arrows X1 and X2 in the drawings. In addition, directions which intersect the sliding directions X1 and X2 of the cover member 20 are indicated by arrows Y1 and Y2 in the drawings, and upper and lower directions of the tube joining device 1 are indicated by arrows Z1 and Z2 in the drawings. In this embodiment, as illustrated in FIG. 1, the directions Y1 and Y2, which intersect the sliding directions X1 and X2 of the cover member 20, are substantially orthogonal to the sliding directions X1 and X2, and correspond to a disposition direction (extension direction) of the tubes T1 and T2.

Figure 2:
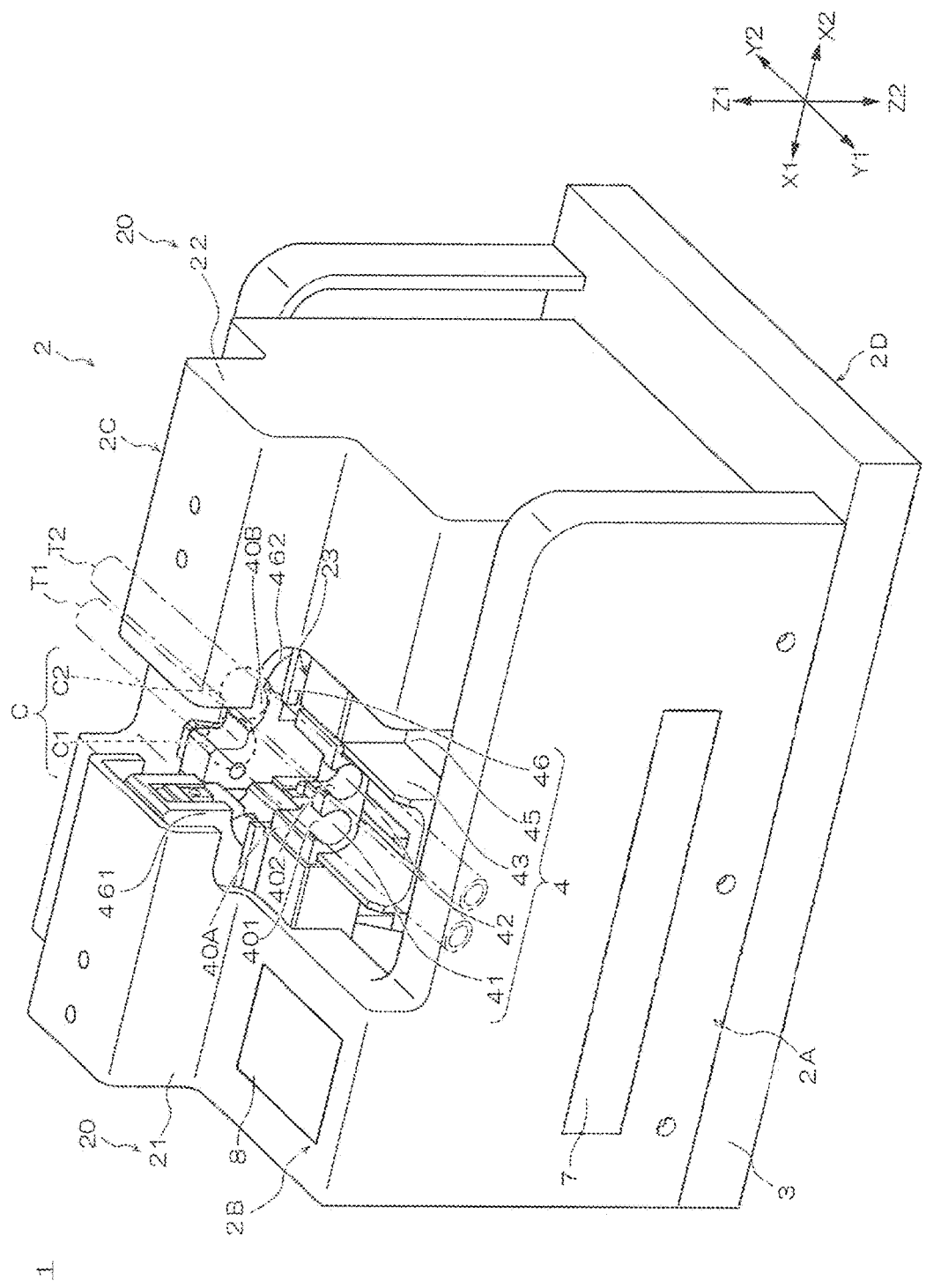
FIG. 2 is a perspective view illustrating a front surface side of the tube joining device to explain the course of closing a cover member.
Figure 3:
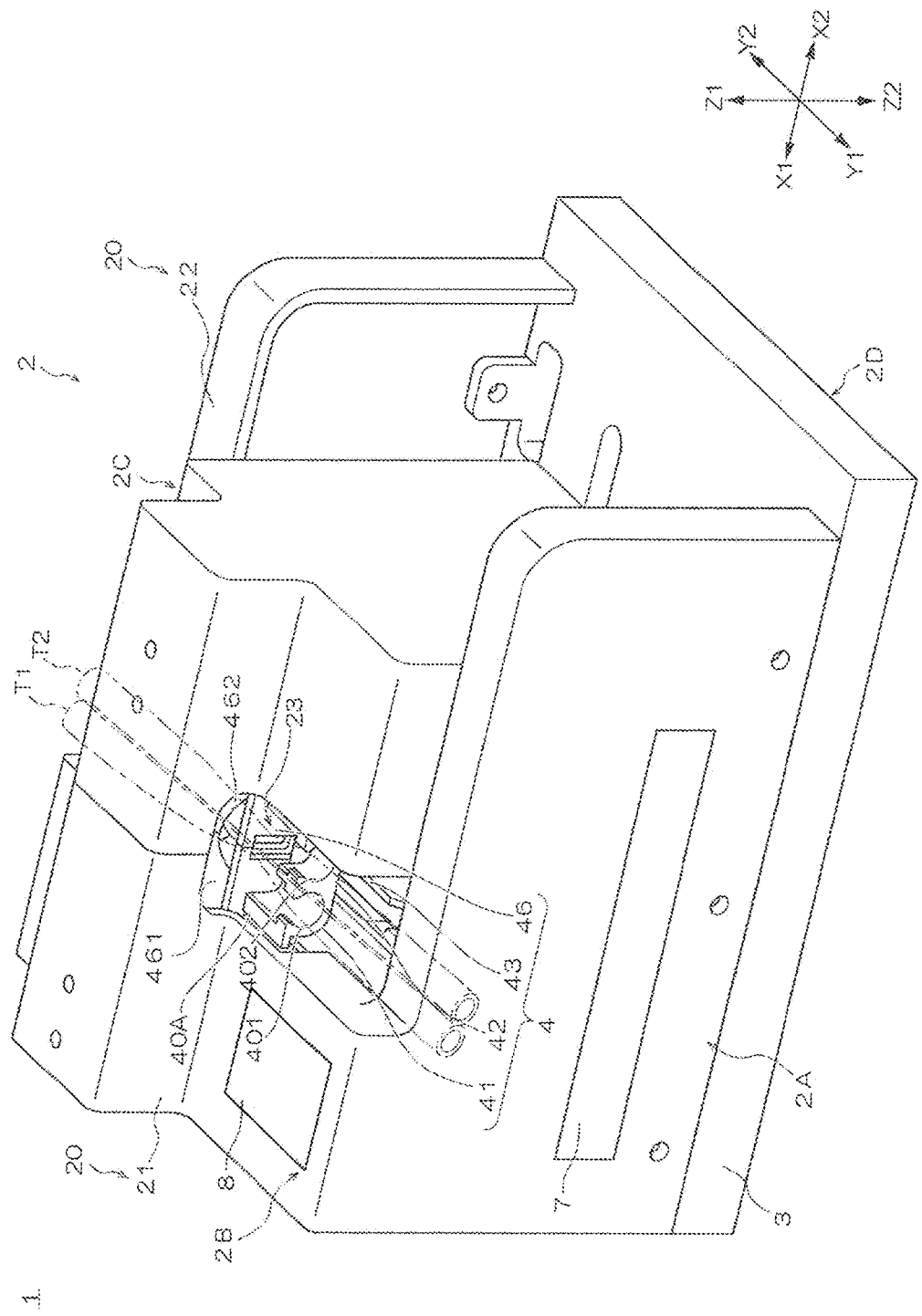
FIG. 3 is a perspective view illustrating the front surface side of the tube joining device in a state in which the cover member is closed.
Figure 4:
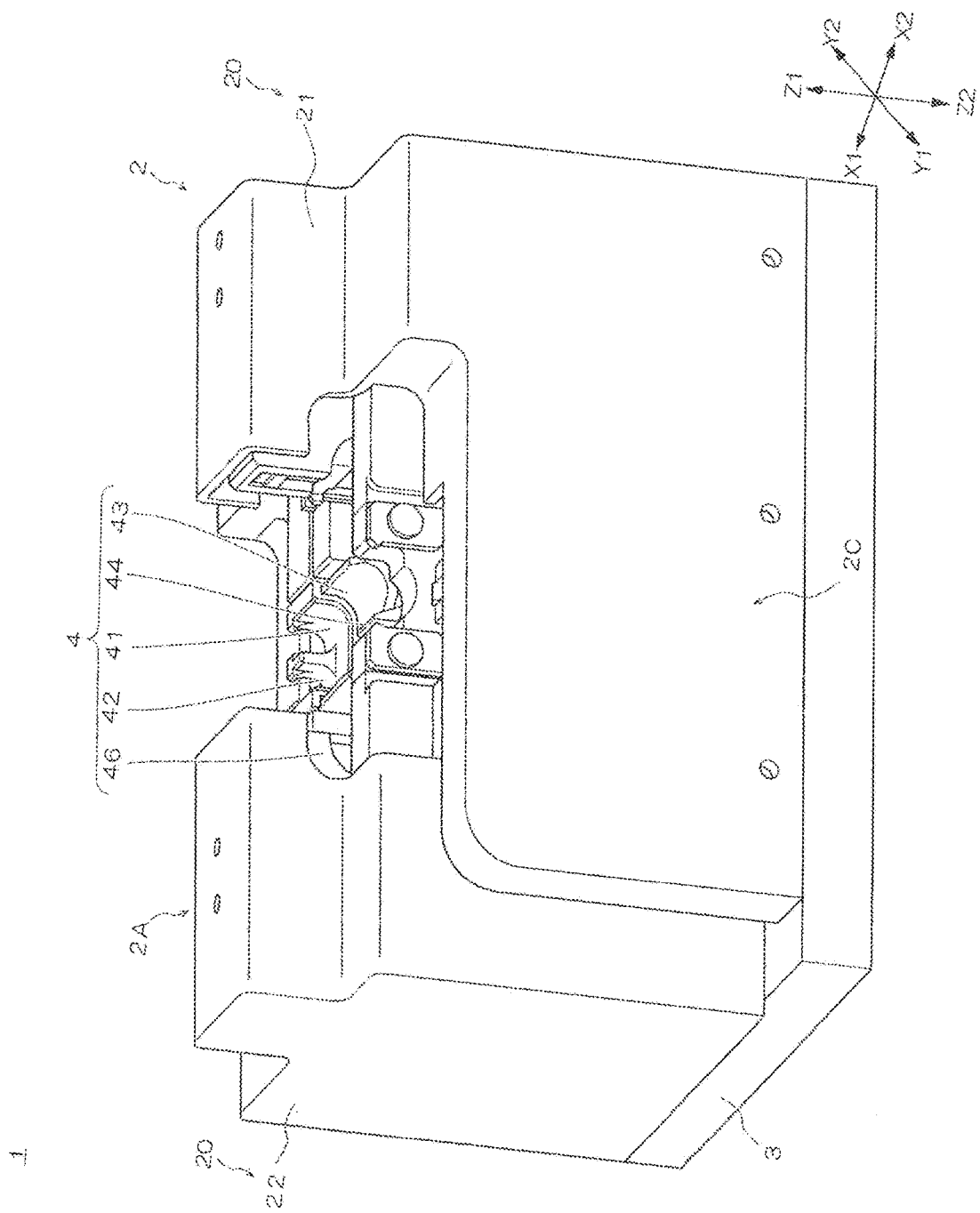
FIG. 4 is a perspective view illustrating a rear surface side of the tube joining device in a state in which the cover member is opened.

As illustrated in FIG. 2 and FIG. 3, when the cover member 20 is closed, a gap 23 is formed between the first pressing member 21 and the second pressing member 22 until the cover member 20 is closed. A user can visually confirm a setting position of the tubes T1 and T2 through the gap 23 until the cover member 20 is closed. According to this, the user can easily and appropriately perform setting of the tubes T1 and T2 which become a joining target, and it is possible to prevent occurrence of a joining failure caused by a setting error of the tubes in advance.

As illustrated in FIG. 1, the tube holding section 4 includes the first tube holding portion 41 that can hold the first tube T1, and the second tube holding portion 42 that is disposed adjacent to the first tube holding portion 41 and can hold the second tube T2 at a position that is parallel to the first tube T1. The first tube holding portion 41 and the second tube holding portion 42 are disposed between the first pressing member 21 and the second pressing member 22.

The tube holding section 4 includes a first accommodation member 40A and a second accommodation member 40B which respectively accommodate the tubes T1 and T2, a joining site holding portion 43 that holds a fusing-joining site C of each of the first tube T1 and the second tube T2, a partition portion 44 that is disposed between a fusing-joining site C1 of the first tube T1 and a fusing-joining site C2 on the second tube T2 side, a support member 45 that supports the first tube holding portion 41 and the second tube holding portion 42 (refer to FIG. 9), and a clamp portion 46 that holds the tubes T1 and T2 so as not to cause positional deviation previous to execution of joining work.

The first accommodation member 40A includes a first holding groove 401 that holds the first tube T1, and a second holding groove 402 that holds the second tube T2. The first holding groove 401 and the second holding groove 402 have a substantially U-shaped cross-section.

The second accommodation member 40B is disposed with a predetermined gap with respect to the first accommodation member 40A in the directions Y1 and Y2 which intersect the sliding directions X1 and X2 of the cover member 20.

The joining site holding portion 43 has a guide function of allowing work of setting the tubes T1 and T2 in the first accommodation member 40A and the second accommodation member 40B to be simply performed. The joining site holding portion 43 is disposed on a lower side of the first accommodation member 40A to be relatively movable with respect to the first accommodation member 40A in the disposition (extension) directions (Y1 and Y2 directions) of the tubes T1 and T2. The joining site holding portion 43 is configured to be relatively movable in synchronization with an opening and closing operation of the housing 2, with respect to the first accommodation member 40A in the disposition direction (Y1 and Y2 directions) of the tubes T1 and T2. The joining site holding portion 43 includes a cut-away portion 431 through which the partition portion 44 can be inserted.

Figure 9:
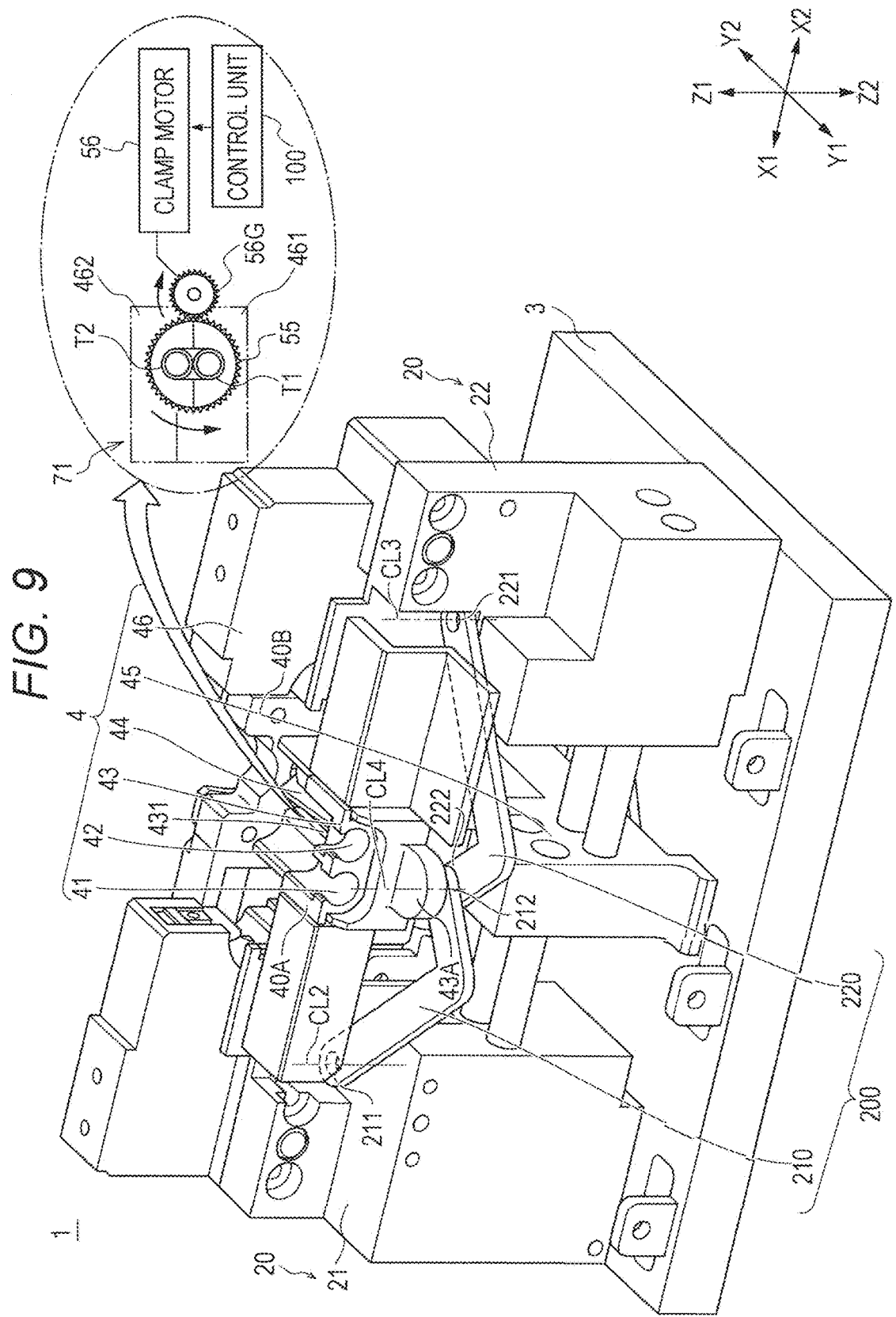
FIG. 9 is a perspective view illustrating a second link mechanism and main portions of the tube joining device in a state in which the cover member is opened.
Figure 12:
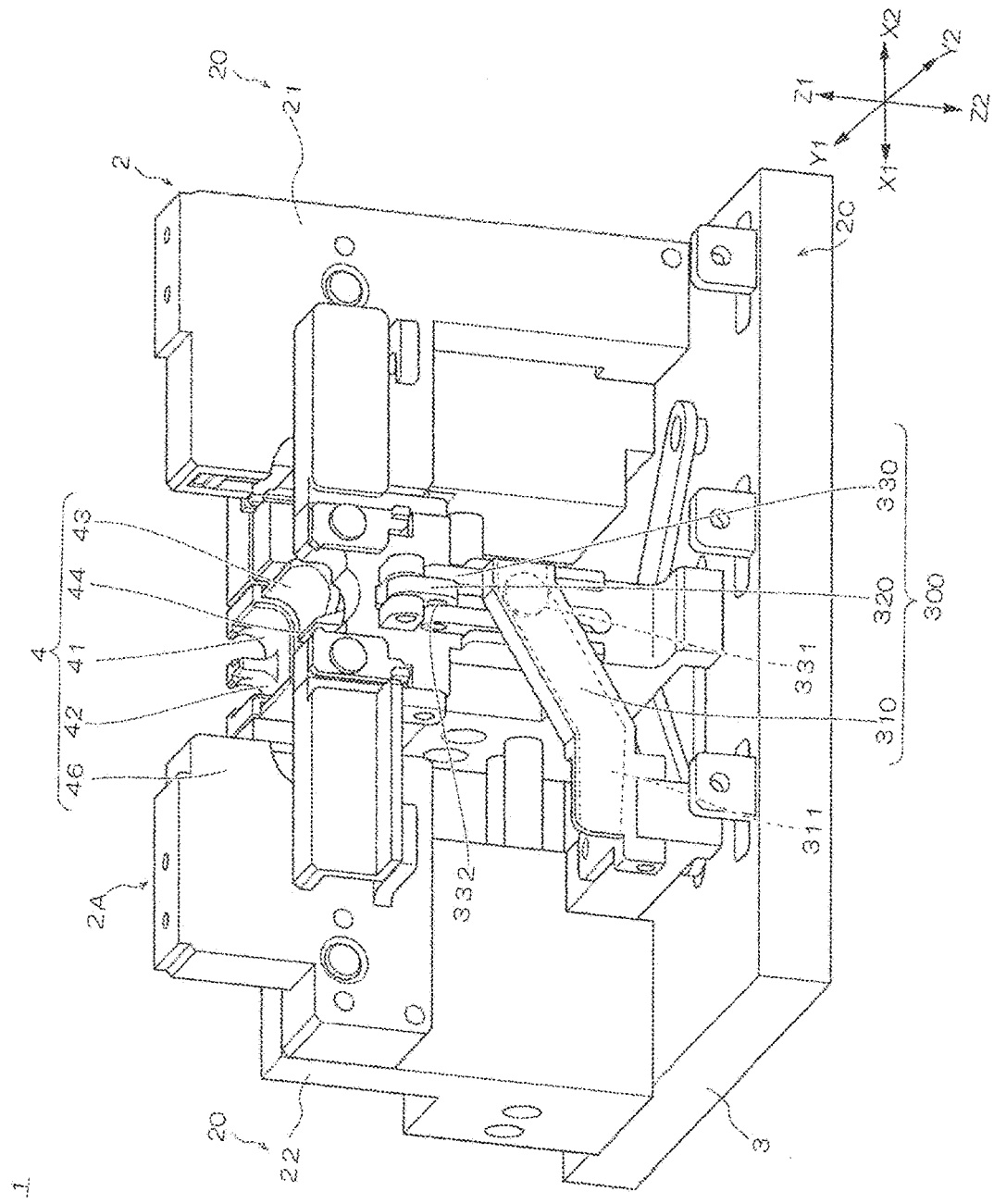
FIG. 12 is a perspective view illustrating a third link mechanism and main portions of the tube joining device in a state in which the cover member is opened.

As illustrated in FIG. 1, FIG. 9, and FIG. 12, in a state in which the housing 2 is opened, the partition portion 44 is inserted through the cut-away portion 431 of the joining site holding portion 43, and is located on an upper side of the joining site holding portion 43. In this state, the tubes T1 and T2 are disposed, and the tubes T1 and T2 are partitioned by the partition portion 44. Accordingly, it is possible to prevent a work error such as setting of the tubes T1 and T2 in a distorted state from occurring.

As illustrated in FIG. 9, the support member 45 is placed on the base 3, and supports the first accommodation member 40A from a lower side. As illustrated in FIG. 6, a first jig 451 and a second jig 452 which extend in the sliding directions X1 and X2 of the cover member 20 are provided in the support member 45. The first jig 451 is inserted into a hole 21A provided in the first pressing member 21 to realize approaching movement of the support member 45 with respect to the first pressing member 21. The second jig 452 is inserted into a hole 21B provided in the first pressing member 21 to realize approaching movement of the support member 45 with respect to the first pressing member 21.

In addition, as illustrated in FIG. 6, a sliding groove 45A that extends in the directions Y1 and Y2 which intersect the sliding directions X1 and X2 of the cover member 20 is provided in the support member 45. The sliding groove 45A has a function of guiding a movement direction of a third support portion 133 of a first link mechanism 100 of the housing 2.

Figure 14:
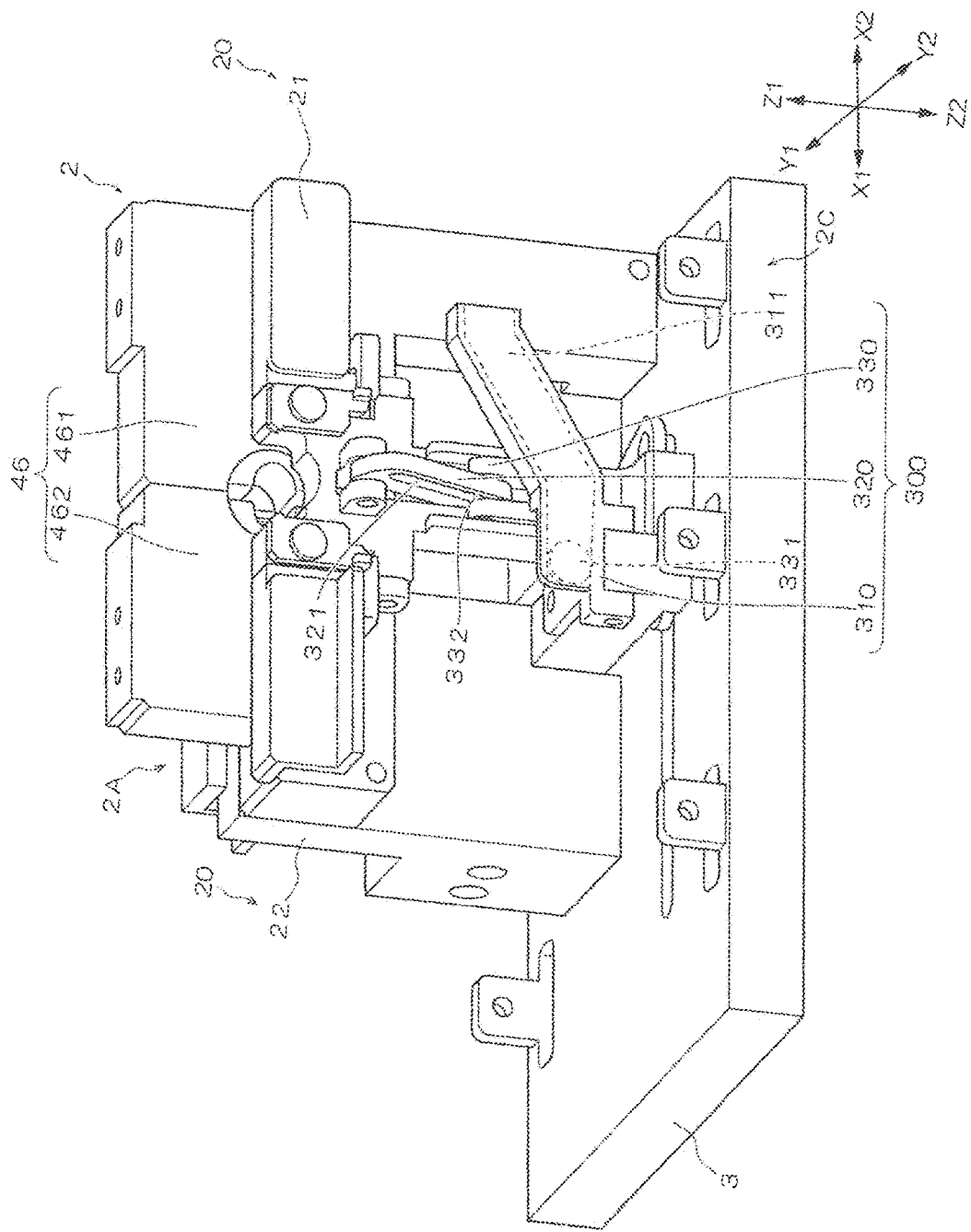
FIG. 14 is a perspective view illustrating the third link mechanism and main portions of the tube joining device in a state in which the cover member is closed.

As illustrated in FIG. 14, the clamp portion 46 includes a first clamp portion 461 that is provided in the first pressing member 21, and a second clamp portion 462 that is provided in the second pressing member 22. The first clamp portion 461 and the second clamp portion 462 are disposed at positions which face each other.

As illustrated in FIG. 6, the housing 2 further includes a first link mechanism 100 that causes the first tube holding portion 41 and the second tube holding portion 42 to approach or to be separated from the first pressing member 21 in synchronization with approach and separation of the first pressing member 21 and the second pressing member 22.

When causing the first tube holding portion 41 and the second tube holding portion 42 to approach or to be separated from the first pressing member 21, the first link mechanism 100 maintains the position of the first tube holding portion 41 and the second tube holding portion 42 at substantially the center PC between the first pressing member 21 and the second pressing member 22.

Hereinafter, the configuration of the first link mechanism 100 will be described in detail with reference to FIG. 6 to FIG. 8.

As illustrated in FIG. 6, the first link mechanism 100 includes a first link member 110 of which one end 111 is connected to the base 3 through a first support portion 131, and a second link member 120 of which one end 121 is fixed to the second pressing member 22 through a second support portion 132.

The first support portion 131 supports the first link member 110 to rotate around a central axis CL1 (rotation axis).

A sliding groove 31 that extends in the sliding directions X1 and X2 along which the first pressing member 21 and the second pressing member 22 approach or are separated from each other is provided in the base 3. The sliding groove 31 has a function of guiding a movement direction of the second support portion 132 of the first link mechanism 100 of the housing 2.

The second support portion 132 slides along the sliding groove 31 provided in the base 3 to move along the sliding directions X1 and X2.

The other end 112 of the first link member 110 and the other end 122 of the second link member 120 are connected by the third support portion 133.

The third support portion 133 is configured to move along the directions Y1 and Y2 which intersect the sliding directions X1 and X2 of the cover member 20 by sliding along the sliding groove 45A provided in the support member 45 of the tube holding section 4. In addition, the first link member 110 and the second link member 120 are disposed on the same plane to be symmetry with respect to the center PC.

Figure 7:
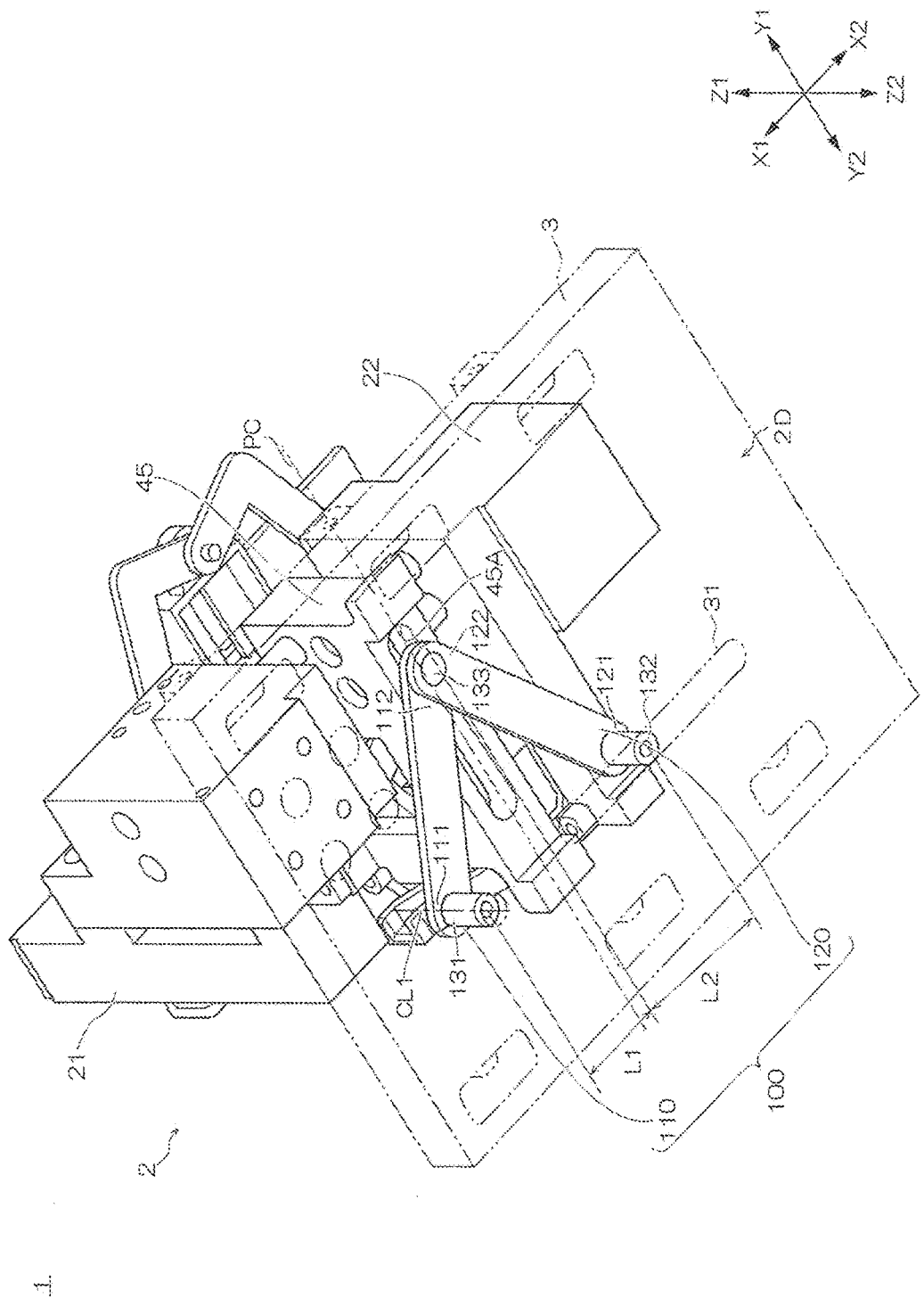
FIG. 7 is a perspective view illustrating the first link mechanism and main portions of the tube joining device in the course of closing the cover member.
Figure 8:
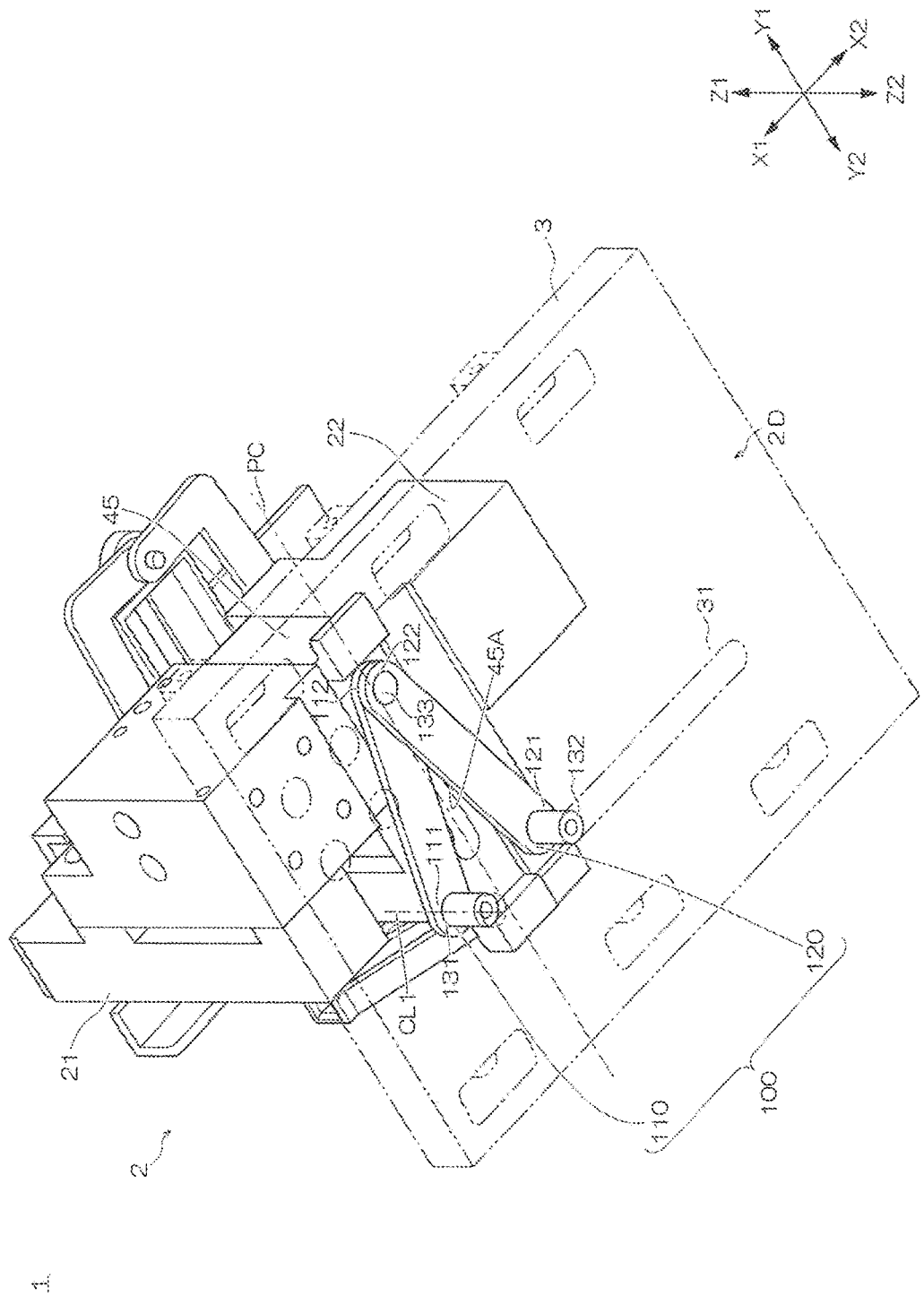
FIG. 8 is a perspective view illustrating the first link mechanism and main portions of the tube joining device in a state in which the cover member is closed.

When moving the second pressing member 22 in the direction X1 of approaching the first pressing member 21 from a state in which the housing 2 is opened as illustrated in FIG. 6, the second support portion 132 slides along the sliding groove 31 of the base 3 and moves in the X1 direction as illustrated in FIG. 7 and FIG. 8. At this time, the third support portion 133 slides along the sliding groove 45A of the support member 45 and moves in the Y1 direction while pressing and moving the tube holding section 4 in the X1 direction through the sliding groove 45A of the support member 45. During the operation, the first link member 110 and the second link member 120 are disposed to be symmetry with respect to the center PC. According to this, a distance L1 between the first support portion 131 and the third support portion 133 along the sliding directions X1 and X2 of the cover member 20, and a distance L2 between the second support portion 132 and the third support portion 133 along the sliding directions X1 and X2 of the cover member 20 become the same as each other (refer to FIG. 7). Accordingly, when the first pressing member 21 and the second pressing member 22 move, the first link mechanism 100 can maintain the position of the first tube holding portion 41 and the second tube holding portion 42 at substantially the center PC between the first pressing member 21 and the second pressing member 22.

In addition, when moving the second pressing member 22 in the direction (X1 direction) of approaching the first pressing member 21 from the state in which the housing 2 is opened as illustrated in FIG. 1, the second clamp portion 462 approaches the first clamp portion 461 as illustrated in FIG. 2. In addition, when the second pressing member 22 is moved in the direction (X1 direction) of approaching the first pressing member 21 and the housing 2 is closed, as illustrated in FIG. 3, the clamp portion 46 holds the tubes T1 and T2 and compresses the tubes T1 and T2 in a direction of approaching each other. When the first pressing member 21 and the second pressing member 22 relatively move during the operation of closing the housing 2, the first link mechanism 100 maintains the position of the first tube holding portion 41 and the second tube holding portion 42 at substantially the center PC between the first pressing member 21 and the second pressing member 22, and thus it is possible to uniformly compress the first tube T1 and the second tube T2 from the sliding directions X1 and X2 of the cover member 20.

The housing 2 further includes a second link mechanism 200 that retracts the joining site holding portion 43 from a space between the first pressing member 21 and the second pressing member 22 in synchronization with approach and separation of the first pressing member 21 and the second pressing member 22.

Hereinafter, a configuration of the second link mechanism 200 will be described in detail with reference to FIG. 9 to FIG. 11.

As illustrated in FIG. 9, the second link mechanism 200 includes a first link member 210 of which one end 211 is connected to the first pressing member 21 to rotate around the central axis CL2, and a second link member 220 of which one end 221 is connected to the second pressing member 22 to rotate around a central axis CL3. The other end 212 of the first link member 210 and the other end 222 of the second link member 220 are connected to a protrusion 43A that is provided at substantially the center PC of the joining site holding portion 43 to rotate around a central axis CL4.

As illustrated in FIG. 9, in a state in which the housing 2 is opened, the joining site holding portion 43 is disposed at the fusing-joining sites C of the tubes T1 and T2. According to this, when setting the tubes T1 and T2 in the tube holding section 4, it is possible to support the tubes T1 and T2 by the joining site holding portion 43, and thus it is possible to prevent the tubes T1 and T2 from being bent or distorted at the fusing-joining sites C.

Figure 10:
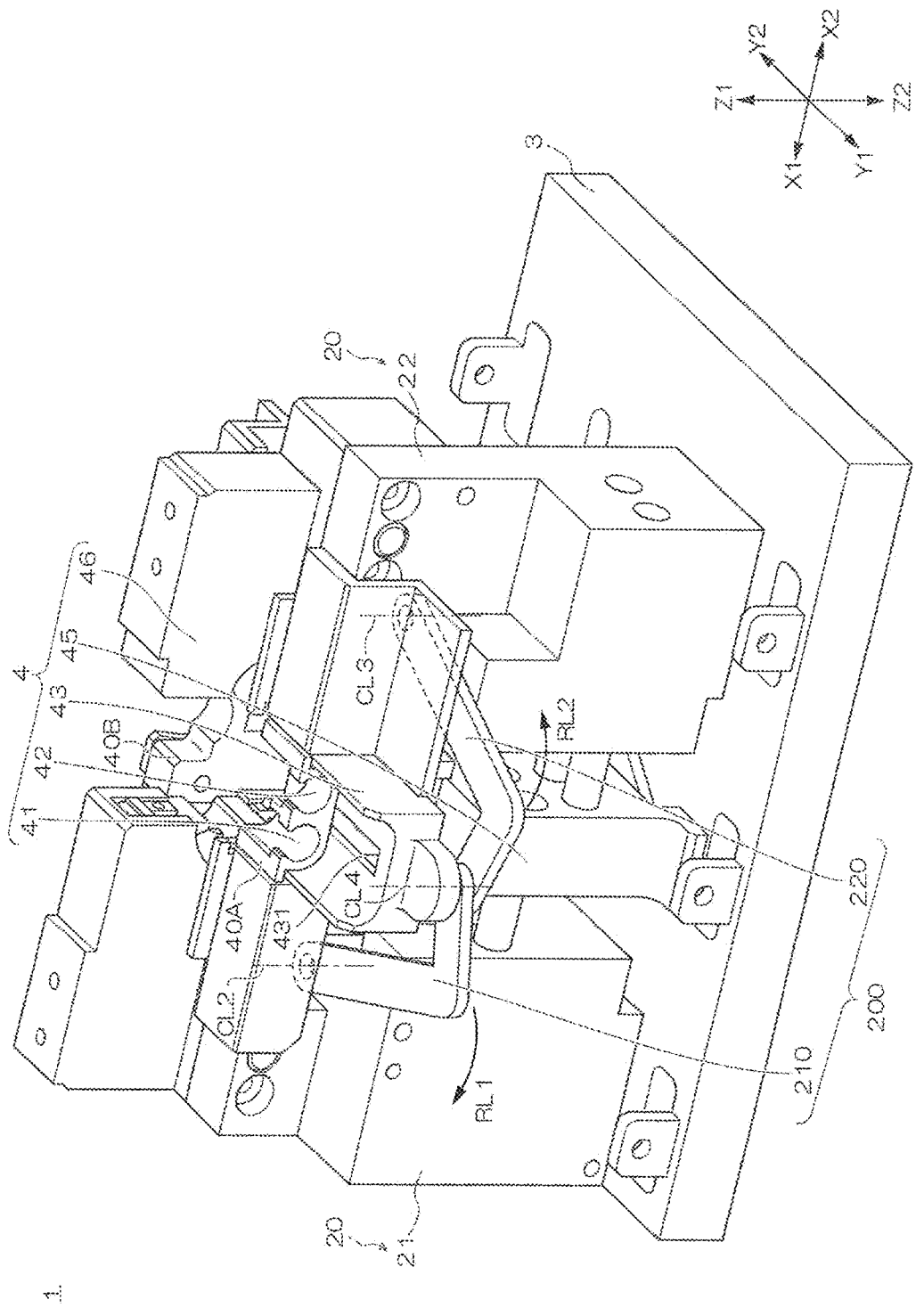
FIG. 10 is a perspective view illustrating the second link mechanism and main portions of the tube joining device in the course of closing the cover member.

As illustrated in FIG. 10, when the second pressing member 22 is moved in the direction (X1 direction) of approaching the first pressing member 21, the first link member 210 rotates around the central axis CL2 in an arrow RL1 direction. Similarly, the second link member 220 rotates around the central axis CL3 in an arrow RL2 direction. When the first link member 210 and the second link member 220 rotate, the joining site holding portion 43 is drawn in the Y1 direction.

Figure 11:
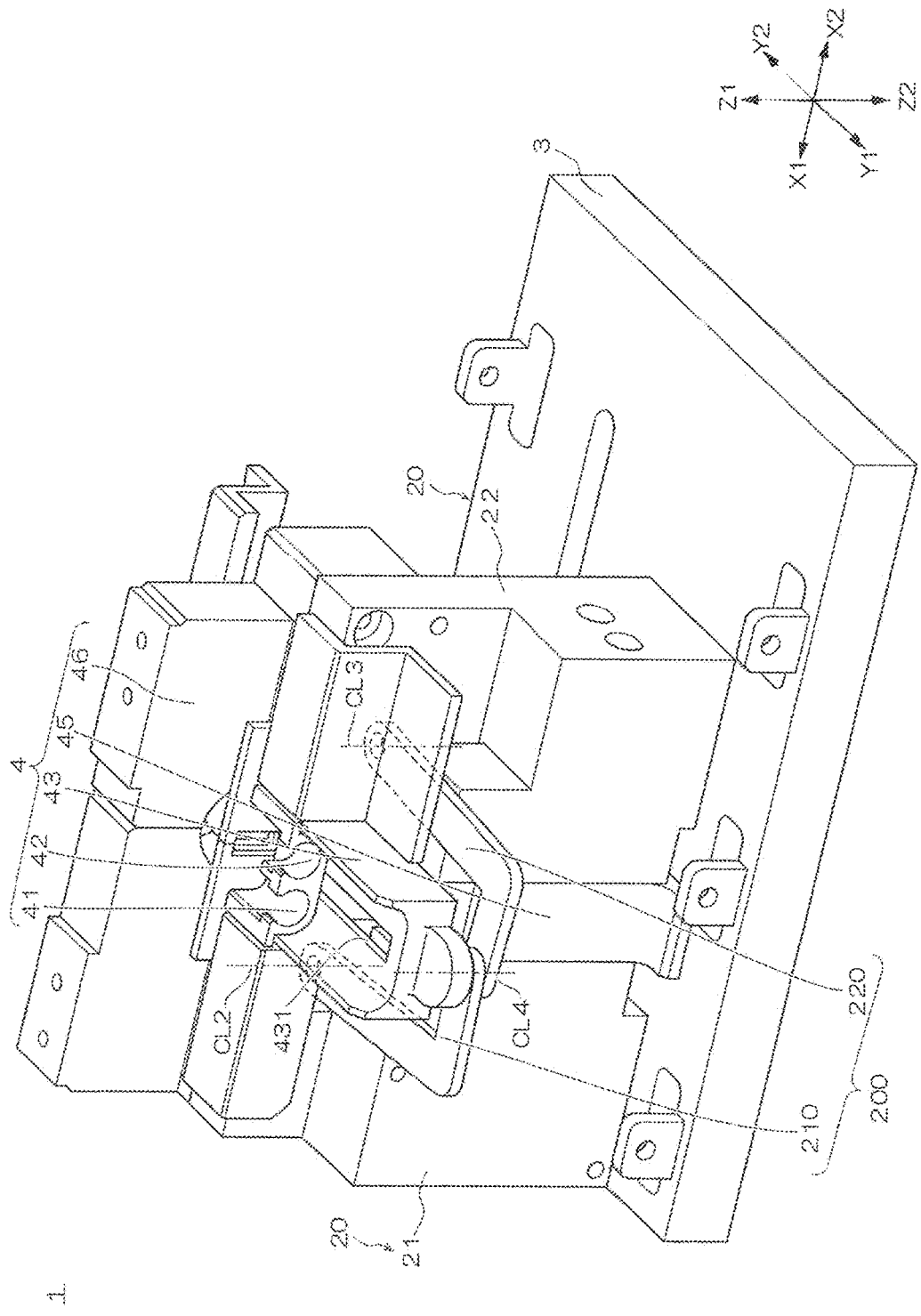
FIG. 11 is a perspective view illustrating the second link mechanism and main portions of the tube joining device in a state in which the cover member is closed.

As illustrated in FIG. 11, when the housing 2 is closed, the second link mechanism 200 retracts the joining site holding portion 43 from the fusing-joining sites C (refer to FIG. 1) between the first pressing member 21 and the second pressing member 22. According to this, in the fusing work and joining work of the tubes T1 and T2, the joining site holding portion 43 does not interfere movement of the tubes T1 and T2 or the wafer WF, and thus it is possible to smoothly perform the fusing work and the joining work.

The housing 2 includes a third link mechanism 300 that retracts the partition portion 44 from a space between the first pressing member 21 and second pressing member 22 in synchronization with the approaching movement of the first pressing member 21 and the second pressing member 22.

Hereinafter, a configuration of the third link mechanism 300 will be described in detail with reference to FIG. 12 to FIG. 14.

As illustrated in FIG. 12, the third link mechanism 300 includes a first link member 310 that is connected to the second pressing member 22, a second link member 320 that is connected to the partition portion 44, and a third link member 330 that causes an operation of the first link member 310 to synchronize with an operation of the second link member 320.

The first link member 310 slides in combination with the second pressing member 22 to approach or to be separated from the first pressing member 21. The first link member 310 includes a first sliding groove 311 along which a protrusion 331 provided in the third link member 330 can slide.

Figure 13:
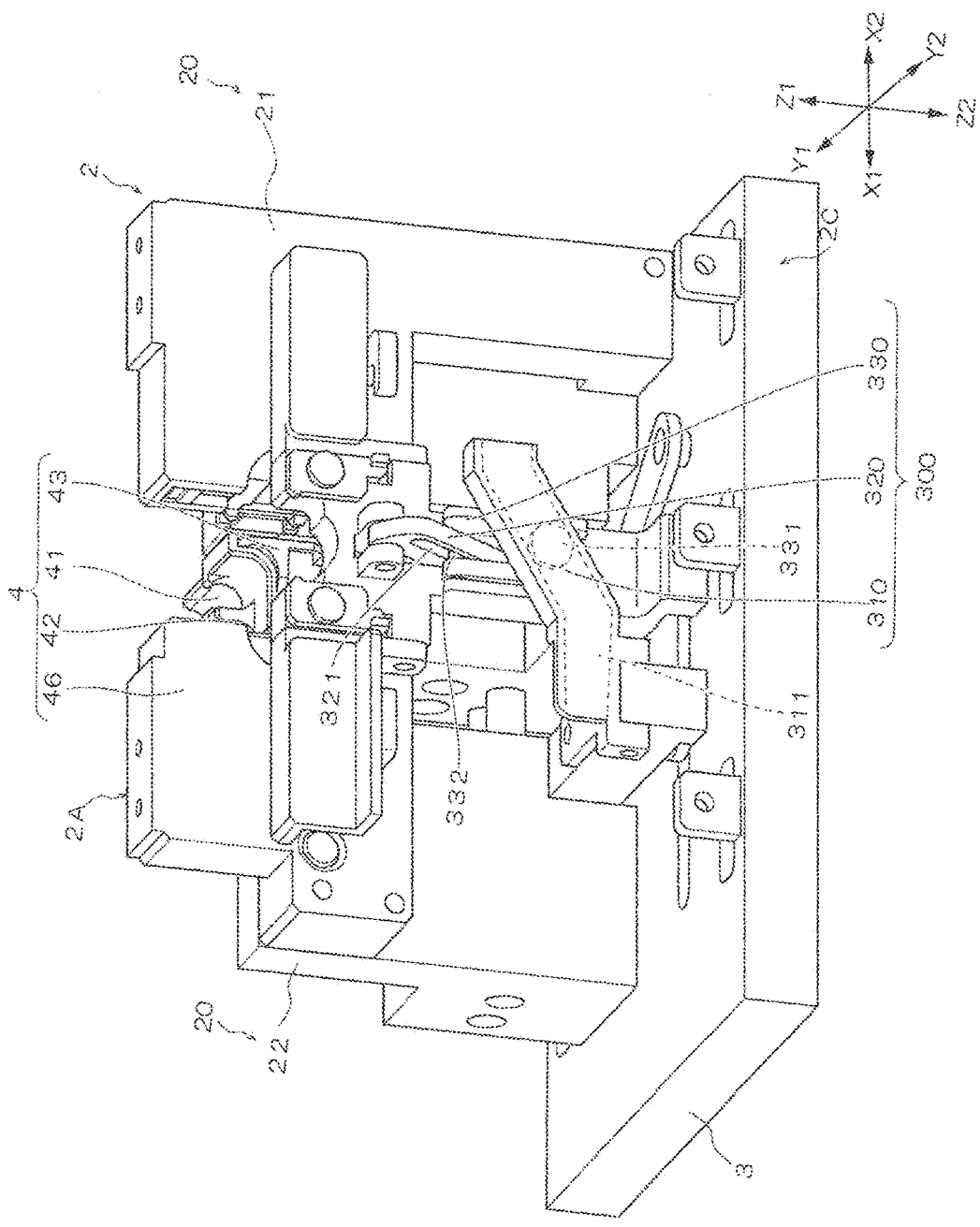
FIG. 13 is a perspective view illustrating the third link mechanism and main portions of the tube joining device in the course of closing the cover member.

As illustrated in FIG. 13, the second link member 320 includes a second sliding groove 321 along which a support portion 332 fixed to the third link member 330 can slide.

When moving the second pressing member 22 in the direction (X1 direction) of approaching the first pressing member 21 from a state in which the housing 2 is opened as illustrated in FIG. 12, the protrusion 331 of the third link member 330 slides along the first sliding groove 311 and moves in a downward direction Z2 as illustrated in FIG. 13. According to this, the support portion 332 fixed to the third link member 330 also slides along the second sliding groove 321 while moving in the downward direction Z2. According to this, the second link member 320 is drawn by the support portion 332 in the downward direction Z2, and the partition portion 44 moves in the downward direction Z2 and is retracted from a space between the tubes T1 and T2. According to this, as illustrated in FIG. 14, in the fusing work and the joining work of the tubes T1 and T2 which are performed after closing the housing 2, the partition portion 44 is not disposed between the tubes T1 and T2, and thus it is possible to smoothly perform the fusing work and the joining work.

Figure 16:
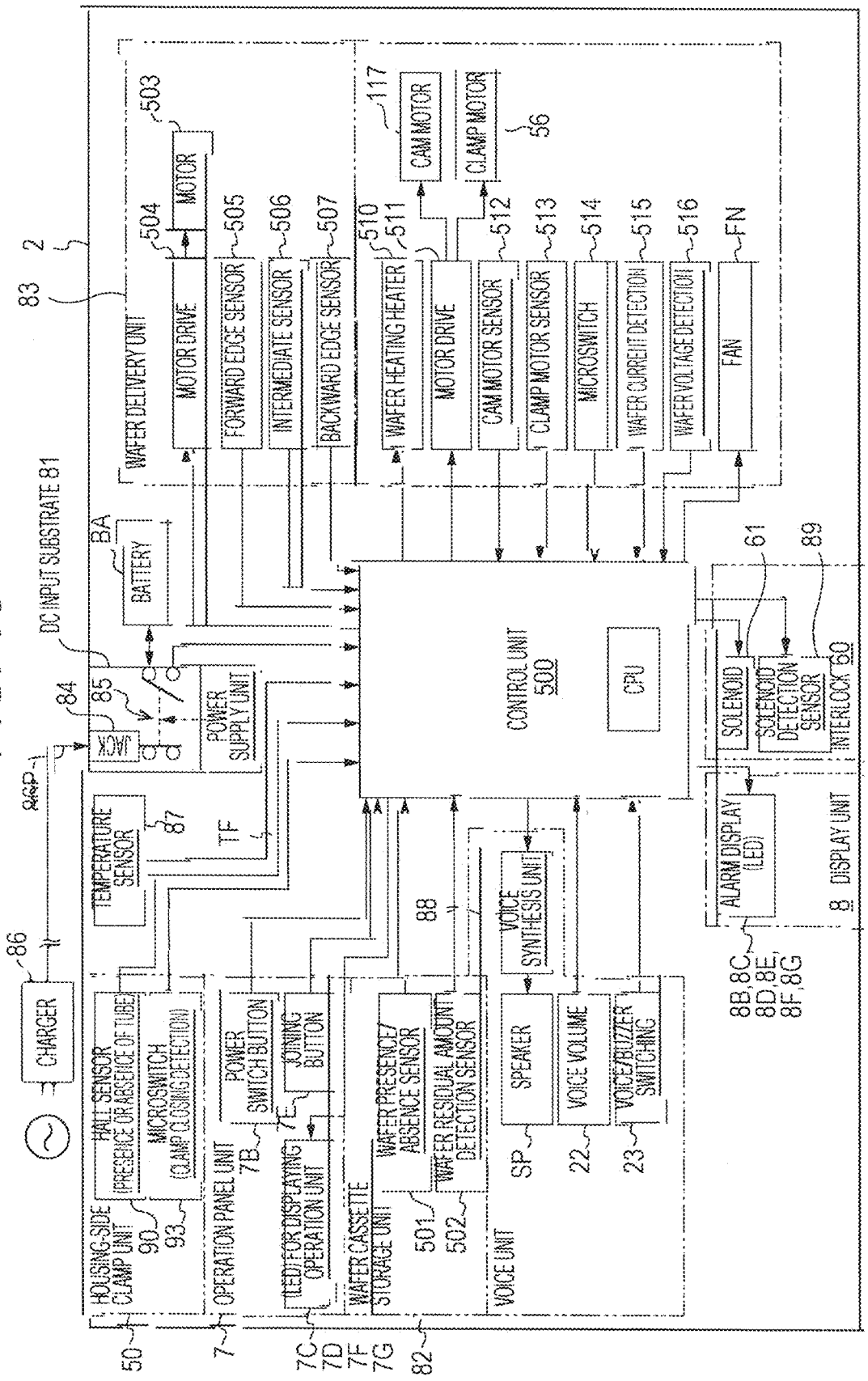
FIG. 16 is a view illustrating an electric block of a control system of the tube joining device.

A speaker SP that emits sound, and a fan FN that discharges a gas inside the housing 2 are disposed on the bottom surface portion 2D of the housing 2 (refer to FIG. 16). The fan FN also has a function as a cooling fan that cools down the wafer WF after terminating a joining operation. In the bottom surface portion 2D of the housing 2, a voice opening that outputs a voice guidance, an alarm sound, and the like which are emitted from the speaker SP to the outside of the housing 2 may be provided, or an exhaust opening for compulsorily discharging heat generated inside the housing 2 or a gas that passes through the inside of the housing 2 to the outside of the housing 2 when the cooling fan FN is operated may be provided.

The housing 2 includes an operation panel unit 7 that includes switches, and a display unit 8. The operation panel unit 7 is disposed on the front surface portion 2A (refer to FIG. 1) of the housing 2 which is located in the direction Y1 that intersects the sliding directions X1 and X2 of the cover member 20. The display unit 8 is disposed on the top surface portion 2B (refer to FIG. 1) of the housing 2 which is located in the upward direction Z1.

Next, the operation panel unit 7 and the display unit 8 will be described with reference to FIGS. 15A to 15B.

Figure 15A:
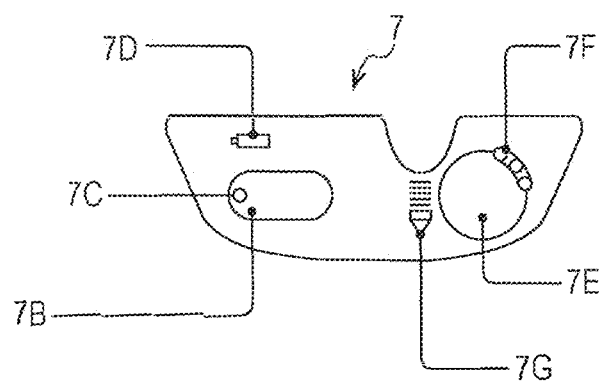
FIG. 15A is a view illustrating a configuration example of an operation panel unit that is provided on a front surface portion side of a housing illustrated in FIG. 1.

As illustrated in FIG. 15A, the operation panel unit 7 includes a [power] switch button 7B, [power] lamp 7C, a [in-charging] lamp 7D, a [joining] button 7E, a [joining] lamp 7F, and a [wafer ejecting] lamp 7G.

The [power] lamp 7C, the [in-charging] lamp 7D, the [joining(welding)] lamp 7F, and the [wafer ejecting] lamp 7G are display lamps indicating various states in the operation panel unit 7. For example, the respective lamps can be constituted by a green light-emitting diode (LED) lamp.

The [power] switch button 7B is a button that is pressed to supply power to the tube joining device 1. The [power] lamp 7C is lightened when pressing the [power] switch button 7B.

The [joining] button 7E is a button that is pressed when a user initiates fusing-joining work of fusing ends of the two tubes T1 and T2 and replacing and pressure-joining the ends of the tubes T1 and T2. The [joining] lamp 7F is lightened when the [joining] button 7E is pressed. In addition, the [joining] lamp 7F may be configured to be flickered to give an alarm of a failure state to a user at the time of failure of the tube joining device 1.

The [in-charging] lamp 7D is lightened in a case where charging with respect to a battery BA from a commercial AC power side is performed.

The [wafer ejecting] lamp 7G is lightened or flickered when joining between the two tubes T1 and T2 is terminated and it enters a state in which a user can eject from the housing 2 the wafer WF that has been used and discharge the wafer WF.

Figure 15B:
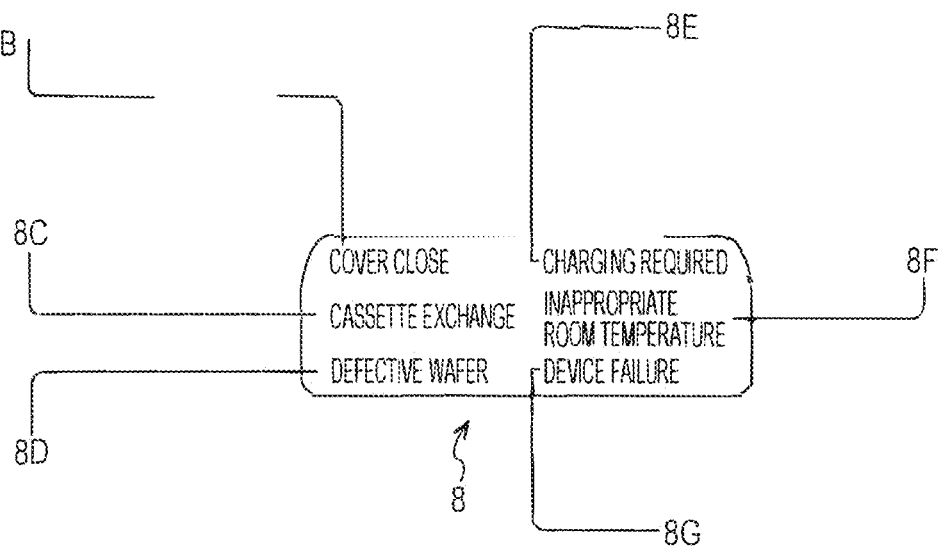
FIG. 15B is a view illustrating a configuration example of a display unit that is provided on a top surface portion of the housing illustrated in FIG. 1.

As illustrated in FIG. 15B, the display unit 8 includes a [cover close] lamp 8B, a [wafer cassette exchange] lamp 8C, a [defective wafer] lamp 8D, a [charging required] lamp 8E, an [inappropriate room temperature] lamp 8F, and a [device failure] lamp 8G.

The [device failure] lamp 8G is an alarm lamp that gives a notification of failure of the tube joining device 1. For example, the [device failure] lamp 8G can be constituted by a red LED lamp. The other lamps are constituted as an alarm display lamp, and can be constituted by, for example, a yellow LED lamp.

Next, the tubes T1 and T2 which become a joining target will be described with reference to FIG. 18 and FIGS. 19A to 19D.

Figure 18:
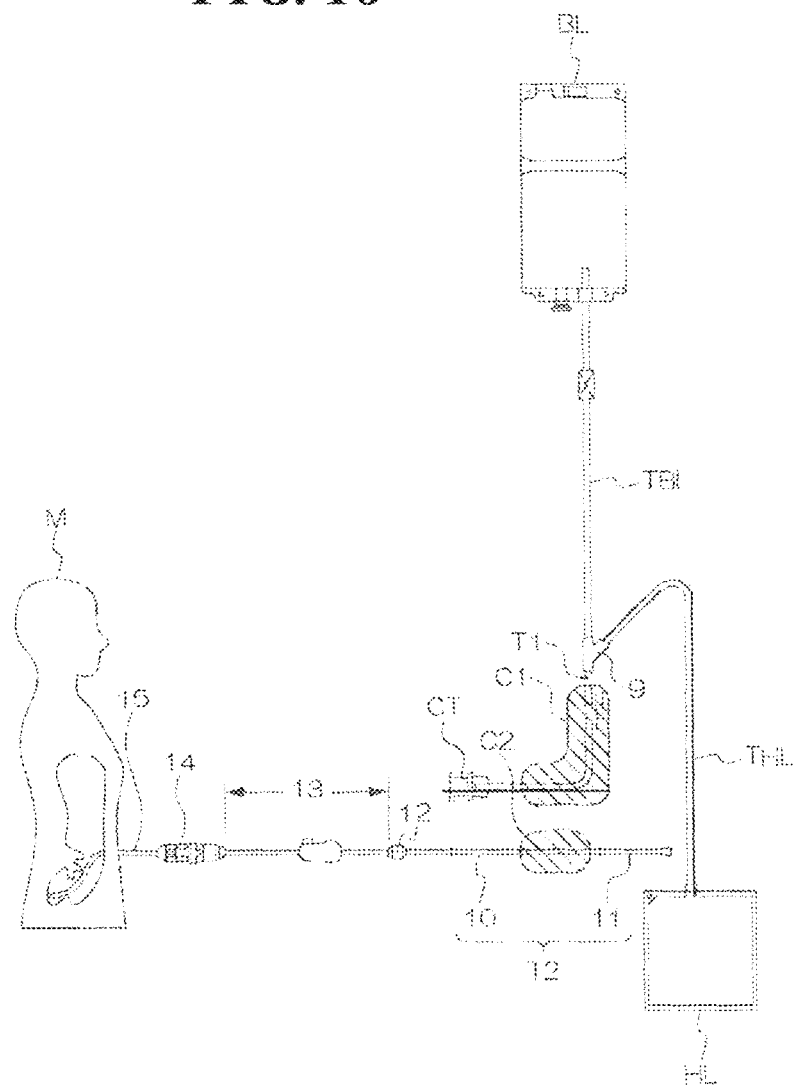
FIG. 18 is a view schematically illustrating tubes which are joined by the tube joining device according to this embodiment.

FIG. 18 illustrates the two tubes T1 and T2 which are joined by the tube joining device 1. As the tubes T1 and T2, for example, a vinyl chloride tube having flexibility can be selected. However, the material of the tubes T1 and T2 is not limited as long as the tubes T1 and T2 can be joined to each other through fusing and pressing. For example, materials of the tubes T1 and T2 may be different from each other.

As illustrated in FIG. 18, a predetermined connector CT is attached to a tip end side of one end of the first tube T1. The other end side of the first tube T1 is connected to a dialysis fluid tube TBL of a dialysis fluid bag BL through a diverging tube 9. In addition, the first tube T1 is connected to a fluid discharge tube THL of a fluid discharge bag HL through the diverging tube 9.

The tube T2 includes an extension tube 10 and a protection tube 11. The extension tube 10 is connected to a peritoneal catheter 15 through a connection tube 12, a silicone tube 13, and a catheter joint 14. One end side of the peritoneal catheter 15 is inserted into an abdominal cavity of a patient M.

Figure 19A:
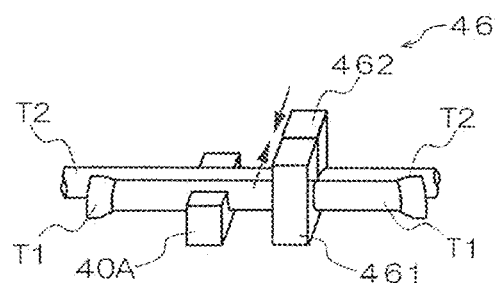
FIG. 19A to FIG. 19D are views schematically illustrating respective processes of fusing-joining work by the tube joining device.
Figure 19B:
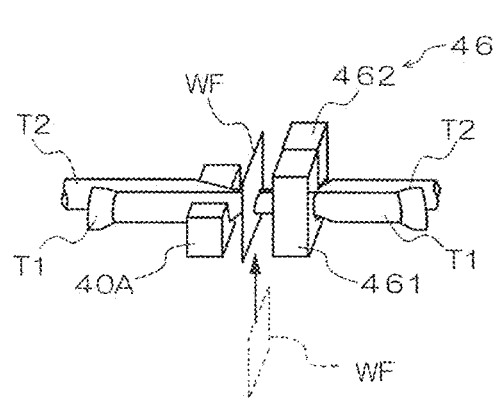

In a state in which a joining site C1 of the first tube T1 and a joining site C2 of the second tube T2 are brought into close contact with each other, the tube joining device 1 fuses the joining sites C1 and C2 by using a heated wafer WF (refer to FIGS. 19A and 19B. In addition, after the fusing, a fused end of the first tube T1 and a fused end of the second tube T2 are replaced, and the ends are pressed and joined (refer to FIGS. 19C and 19D.

In addition, as illustrated in FIG. 6, before carrying out the joining work by the tube joining device 1, the tubes T1 and T2 are held by the first tube holding portion 41 and the second tube holding portion 42 which are provided in the housing 2 so as not to cause positional deviation. In a state in which the clamp portion 46 holds the tubes T1 and T2, when performing work of closing the housing 2 (work of causing the second pressing member 22 to approach the first pressing member 21), the tubes T1 and T2 are set in a state of pressing each other (refer to FIG. 3). After performing the setting, the tubes T1 and T2 are fused by using the heated wafer WF.

Next, a function of a control unit 500 of the tube joining device 1 will be described with reference to FIG. 16. FIG. 16 illustrates an electric block of the tube joining device 1.

The tube joining device 1 includes a control unit 500 that collectively controls operations of respective units of the device. The control unit 500 includes a CPU such as a microcomputer, a ROM that stores a control program of the entirety of the device which is executed by the CPU or various pieces of data, and a RAM that temporarily stores measurement data or various pieces of data as a work area.

The control unit 500 is supplied with power from the battery BA on the DC input substrate 81 side. The DC input substrate 81 includes a jack 84 and a switching switch 85. When being connected to a connection pin 86P of a charger 86, the jack 84 receives a predetermined DC power that is AC/DC converted from a commercial AC power supply. Furthermore, the charger 86 and the jack 84 are also illustrated in FIG. 1.

The switching switch 85 connects the jack 84 and the battery BA. DC power from the charger 86 can be used in charging of the battery BA. In addition, the DC power charged in the battery BA is supplied to the control unit 500.

A temperature sensor 87 such as a thermistor is electrically connected to the control unit 500. The temperature sensor 87 detects an environment temperature (outside air temperature) around the housing 2, and supplies outside air temperature information TF to the control unit 500. When heating the tubes T1 and T2, the control unit 500 refers to the outside air temperature information TF, and for example, in a case where the outside air temperature is lower than a temperature that is determined in advance, the control unit 500 executes processing of lengthening a heating time of the two tubes T1 and T2. In addition, for example, the control unit 500 performs operation control so that a patient is notified of the environment temperature with the speaker SP.

As illustrated in FIG. 16, the [power switch] button 7B, the [joining] button 7E, and the lamps 7C, 7D, 7F, and 7G of the operation panel unit 7 which are illustrated in FIG. 15A are electrically connected to the control unit 500.

The speaker SP is electrically connected to the control unit 500 through a voice synthesis unit 88. The speaker SP emits, for example, a voice guidance that is determined in advance in accordance with a command of the control unit 500.

A voice adjusting volume 26 and a voice/message switching switch 27 are electrically connected to the control unit 500. In a case where the voice/message switching switch 27 is "turned on", a voice guidance can be emitted from the speaker SP, and in a case where the voice/message switching switch 27 is "turned off", it is possible to sound a buzzer (not illustrated).

As illustrated in FIG. 1, the [cover close] button 8B, the [wafer cassette exchange] lamp 8C, the [defective wafer] lamp 8D, the [charging required] lamp 8E, the [inappropriate room temperature] lamp 8F, and the [device failure] lamp 8G of the display unit 8 are configured to be lightened or flickered in accordance with a command of the control unit 500.

A hall sensor 90 of the clamp portion 46 is electrically connected to the control unit 500, and is configured to transmit a detection result to the control unit 500. As illustrated in FIG. 18, when the tubes T1 and T2 are inserted into the clamp portion 46, a tube detection pin 75 is pressed to a downward side of the device against a force of the spring 92 due to the first tube T1 and the second tube T2. Due to the pressing, the tube detection pin 75 descends, and thus a magnetic force of a magnet 91 is detected by the hall sensor 90. In addition, the hall sensor 90 transmits a signal for giving a notification that "the two tubes T1 and T2 are correctly inserted" to the control unit 500. In a case where the first tube T1 and the second tube T2 are not reliably held, or only one of the tubes is held, the hall sensor 90 cannot detect the magnetic force of the magnet 91. At this time, the hall sensor 90 transmits a signal for giving a notification that "the two tubes T1 and T2 are not correctly inserted" to the control unit 500. Furthermore, a position of installing the tube detection pin 75 is not limited to the position illustrated in FIG. 18 as long as it is possible to detect whether or not the tubes T1 and T2 are set in the clamp portion 46 at the position.

The clamp portion 46 includes a microswitch 93. The microswitch 93 is a sensor that detects a closed state of the housing 2. When the second pressing member 22 is caused to slide and approach the first pressing member 21 as illustrated in FIG. 6, the microswitch 93 detects that the clamp plate 30 closes the clamp portion 46 as illustrated in FIG. 1. Furthermore, as the microswitch 93, for example, it is possible to use a known sensor such as a mechanic type sensor that detects closing by contact with an arbitrary position of the housing 2 when closing the clamp portion 46, and an electric type sensor that detects closing on the basis of a position of the clamp portion 46.

The wafer cassette storage unit 82 includes a wafer presence/absence sensor 501 and a wafer residual amount detection sensor 502. The wafer presence/absence sensor 501 is a sensor that detects whether or not the wafer WF remains in the wafer cassette WC. The wafer residual amount detection sensor 502 is a sensor that detects how many sheets of wafers WF remain in the wafer cassette WC, that is, the number of sheets of remaining wafer WF. As the wafer presence/absence sensor 501 and the wafer residual amount detection sensor 502, for example, a known photosensor or the like can be used.

The wafer delivery unit 83 is a unit that linearly moves the wafer WF in the wafer cassette WC to a predetermined stand-by position (refer to FIG. 18). The wafer delivery unit 83 includes a motor 503, a motor drive 504, a forward edge sensor 505, an intermediate sensor 506, and a backward edge sensor 507. When receiving a command from the control unit 500, the motor drive 504 drives the motor 503, and linearly moves the wafer in the wafer cassette WC to the stand-by position sheet by sheet.

The control unit 500 is electrically connected to a wafer heating heater 510, a motor drive 511, a cam motor sensor 512, a clamp motor sensor 513, a microswitch 514, a wafer current detection unit 515, a wafer voltage detection unit 516, and the fan FN. When the motor drive 511 receives a command from the control unit 500, the motor drive 511 drives the cam motor 517 or the clamp motor 56 to fuse and join the tubes T1 and T2.

The cam motor 517 performs an operation of vertically moving the wafer WF, and an operation of pressing the two tubes T1 and T2 against each other. The operation of vertically moving the wafer WF by the cam motor 517 is an operation of ascending the wafer WF from the stand-by position to a fusing position PSm on an upward side of the stand-by position, and descending the wafer WF from the fusing position PSm to the stand-by position in a contrast manner (refer to FIGS. 19A to 19D). In addition, the cam motor 517 performs an operation of pressing the tubes T1 and T2 against each other after fusing the two tubes T1 and T2. The pressing operation is an operation of causing the wafer WF to enter a stand-by state by descending the wafer WF from the fusing position PSm to the stand-by position, and of performing joining by pressing an end of the first tube T1 on one side to an end of the second tube T2 on the other side, and pressing an end of the second tube T2 on the one side to an end of the first tube T1 on the other side and performing joining.

The clamp motor 56 performs rotation of the movable clamp unit 72 by 180° and returning rotation after the rotation by 180° (refer to FIGS. 19A to 19D). An operation of the movable clamp unit 72 will be described later.

The cam motor sensor 512 is constituted by, for example, a photosensor that detects a cam position and the original point. The clamp motor sensor 513 is constituted by, for example, a photosensor that detects the original point during rotation of the movable clamp unit 72.

The wafer heating heater 510 is provided to heat a wafer in accordance with a command from the control unit 500. When supplying power, the wafer current detection unit 515 detects a wafer current value that is supplied to the wafer. In addition, the wafer voltage detection unit 516 detects a wafer voltage value that is supplied to the wafer.

Next, the wafer cassette storage unit 82 and the wafer cassette WC will be described with reference to FIGS. 17A and 17B.

Figure 17A:
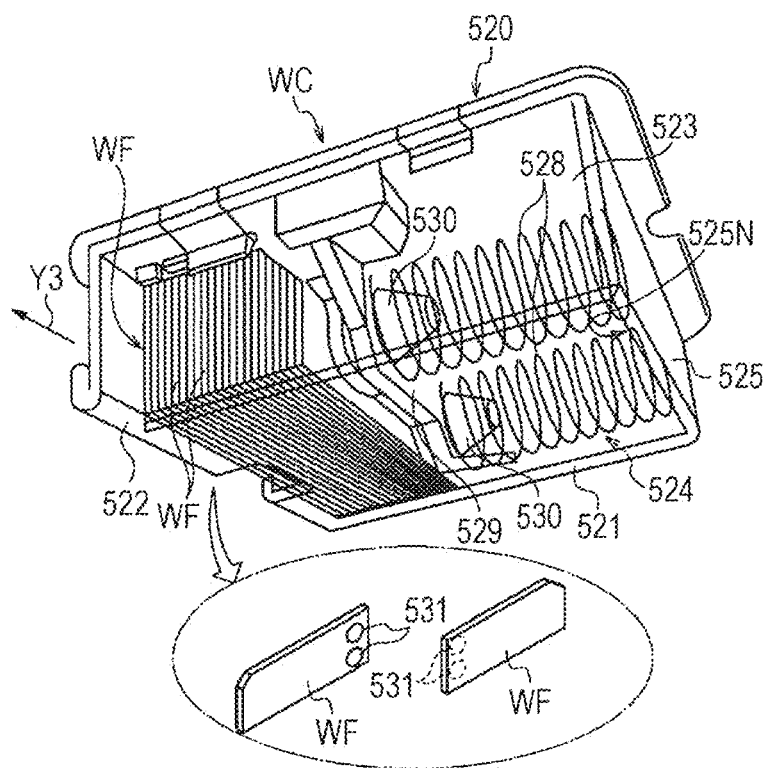
FIG. 17A is a perspective view illustrating a bottom surface portion of a wafer cassette.
Figure 17B:
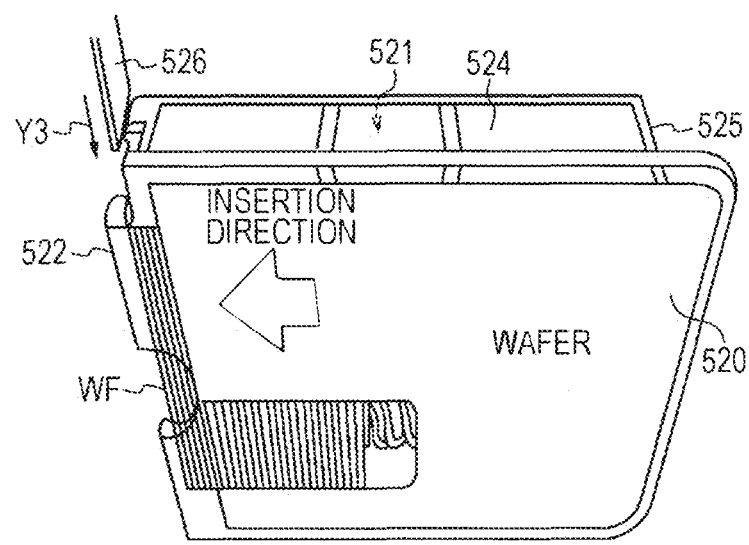
FIG. 17B is a perspective view illustrating a top surface portion of the wafer cassette.

FIG. 17A is a perspective view illustrating a lower surface side of the wafer cassette WC, and FIG. 17B is a perspective view illustrating an upper surface side of the wafer cassette WC.

As illustrated in FIGS. 17A and 17B, the wafer cassette WC is constituted by a container for accommodating a plurality of sheets of the wafers WF. The wafer cassette WC is preferably formed from a transparent plastic to visually confirm an inner side of the wafer WF.

The wafer cassette WC includes a top surface portion 520, a bottom surface portion 521, a front surface portion 522, lateral surface portions 523 and 524, and a bottom surface portion 525.

The wafer WF is disposed sheet by sheet on an inner side of the front surface portion 522. In addition, as illustrated in FIG. 17B, when pressing a pushing member 526 with respect to the wafer WF in a Y3 direction, one sheet of wafer WF is pushed out from the inside of the wafer cassette WC to a predetermined stand-by position along the Y3 direction.

As illustrated in FIGS. 17A and 17B, two springs 528 and a spring accommodation member 529 are accommodated at the inside of the wafer cassette WC. One end of each of the two springs is supported to an inner surface of the bottom surface portion 525 of the wafer cassette WC. On the other hand, the other end of each of the two springs is supported to the spring accommodation member 529. The spring accommodation member 529 includes a positional deviation preventing portion 530 in order for each of the springs 528 not to deviate.

The two springs 528 press a plurality of sheets of the wafers WF against an inner surface of the front surface portion 522 through the spring accommodation member 529. In a state in which the wafers WF are held by the two springs 528, when the pushing member 526 is pressed against the wafer WF located on the front surface portion 522 side in the Y3 direction, only one sheet of the wafer WF located on the outermost side is output from the inside of the wafer cassette WC along the Y3 direction.

As illustrated in FIG. 17A, the wafer WF that can be used as a cutting member is constituted by a copper metal plate (a thickness: approximately 0.3 mm, a width: approximately 34 mm, and a height: approximately 13 mm) that can be heated by the wafer heating heater 510 (refer to FIG. 16 and FIG. 18) and is formed in a substantially rectangular shape. Furthermore, the wafer WF has two contact points 531 which are connected to the wafer heating heater 510 when being heated.

A user sets the tubes T1 and T2 in the tube holding section 4 in using the tube joining device 1. In addition, after closing the housing 2, the user presses the [joining] button 7E illustrated in FIG. 1 to initiate the fusing-joining work by the tube joining device 1. The tube joining device 1 performs the fusing-joining work in a state in which a part of the tubes T1 and T2 is covered with the housing 2.

Referring to FIG. 3, when closing the housing 2, the second clamp portion 462 that is disposed in the second pressing member 22 approaches the first clamp portion 461 that is disposed in the first pressing member 21 to be integrated with each other, thereby forming the movable clamp unit 72 that replaces ends of the tubes T1 and T2 which are fused by the wafer WF. On the other hand, the second clamp portion 462 that is provided in the clamp portion 46 approaches the first clamp portion 461 to be integrated with each other, thereby forming a fixed clamp unit 71 that fixedly holds the tubes T1 and T2 which are fused by the wafer WF.

As is simply illustrated in a broken line portion in FIG. 9, for example, a predetermined gear 55 can be formed at the periphery of the tube holding portion 6. In addition, the gear 55 can be configured to engage with a gear 56G of the clamp motor 56 that drives an operation of replacing positions of ends of the tubes T1 and T2 after fusing the tubes T1 and T2.

For example, when the clamp motor 56 operates by a command of the control unit 500 (refer to FIG. 16) and rotates the gear 56G, the first clamp portion 461 and the second clamp portion 462 positively rotate by 180° in an integrated state. During the rotation, the fused end of the first tube T1 on the other side and the fused end of the second tube T2 on the other side rotate and positions thereof are replaced. According to this, positions of the fused end of the first tube T1 on the other side and the fused end of the second tube T2 on the other side are laterally reversed by 180°. As a result, the end of the first tube T1 on one side and the end of the second tube T2 on the other side can be joined to each other, and the end of the first tube T1 on the other side and the end of the second tube T2 on the one side can be joined to each other.

During rotation of the end of the first tube T1 on the other side and the end of the second tube T2 on the other side by the movable clamp unit 72, the fixed clamp unit 71 that is constituted by the clamp portion 46 holds the end of the first tube T1 on the one side and the end of the second tube T2 on the one side in a position-fixed manner, and prevents the ends from erroneously rotating.

Next, a procedure when using the tube joining device 1 and an operation example of respective portions of the device will be described. In addition, the tubes T1 and T2 are omitted in the drawings.

First, a user sets the housing 2 in an opened state as illustrated in FIG. 1.

Next, the user sets the tubes T1 and T2 in the tube holding section 4.

Next, the user performs an operation of closing the housing 2 as illustrated in FIG. 2 to cause the second pressing member 22 to approach the first pressing member 21 in the approaching direction X1. In synchronization with the approaching movement of the first pressing member 21 and the second pressing member 22, as illustrated in FIG. 2 and FIG. 10, the joining site holding portion 43 moves in the Y1 direction to be retracted from a space between the first pressing member 21 and the second pressing member 22. Similarly, in synchronization with the approaching movement of the first pressing member 21 and the second pressing member 22, the partition portion 44 is retracted from a space between the first pressing member 21 and the second pressing member 22.

Figure 5:
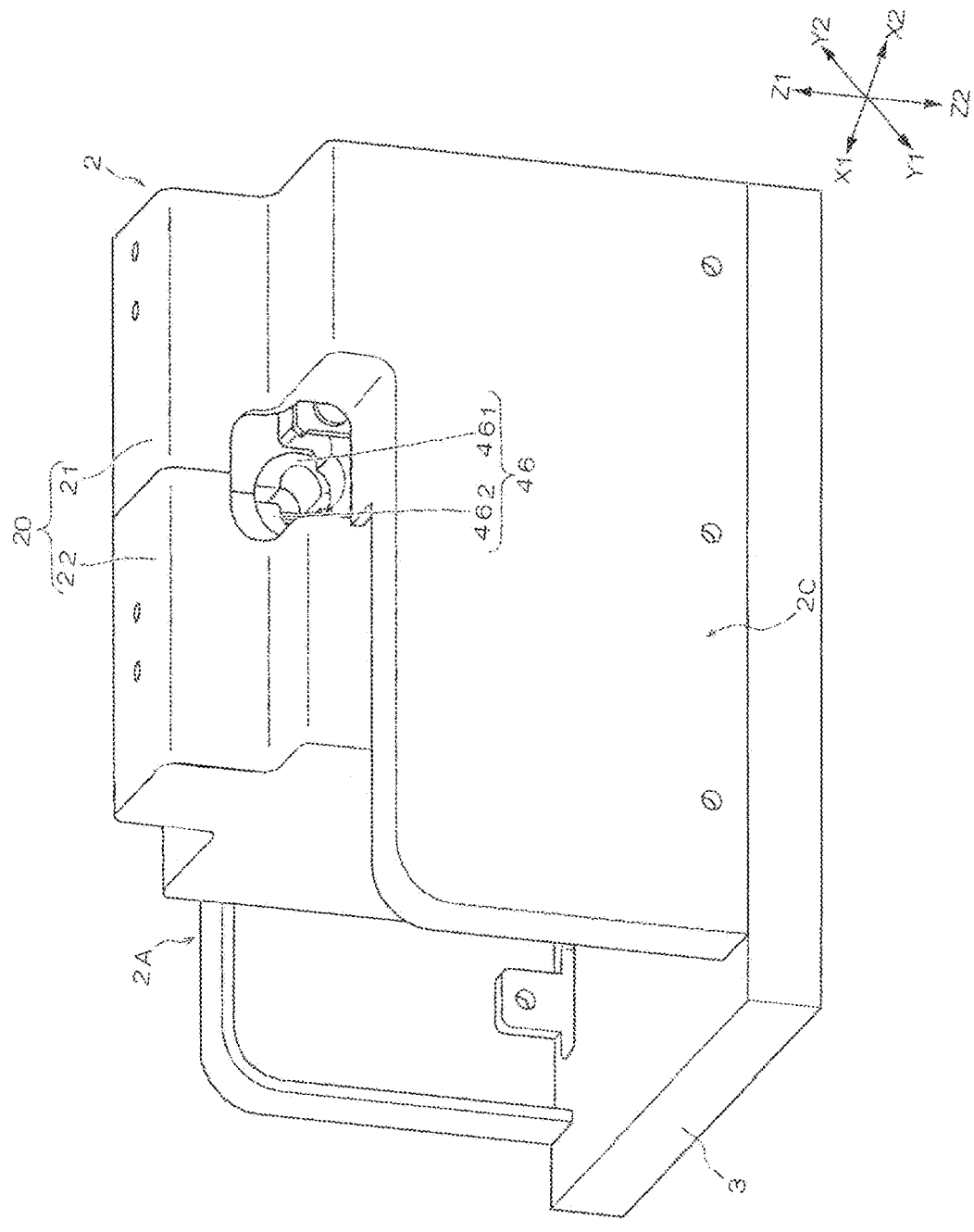
FIG. 5 is a perspective view illustrating the rear surface side of the tube joining device in a state in which the cover member is closed.

Next, the user further causes the second pressing member 22 to approach the first pressing member 21 in the approaching direction X1. According to this, a tube pressing operation by the clamp portion 46 is initiated. In addition, as illustrated in FIG. 3, FIG. 5, and FIG. 19A, when the user closes the housing 2, the first clamp portion 461 and the second clamp portion 462 are integrated with each other. The fusing-joining sites C of the tubes T1 and T2 can be visually confirmed through the gap 23 formed between the first pressing member 21 and the second pressing member 22. According to this, it is possible to visually confirm that the tubes T1 and T2 are correctly set in the tube holding section 4. In addition, the outer periphery of the fusing-joining sites C of the tubes T1 and T2 is covered with the cover member 20, and thus it is possible to perform the fusing and the subsequent joining work in an aseptic condition.

Next, fusing of the tubes T1 and T2 is performed by the heated wafer WF. As illustrated in FIG. 19B, the wafer WF is guided to the fusing-joining sites C of the tubes T1 and T2 from a stand-by position, and passes between the first accommodation member 40A and the clamp portion 46 and fuses the tubes T1 and T2. The wafer WF is returned to the stand-by position after fusing the tubes T1 and T2.

Figure 19C:
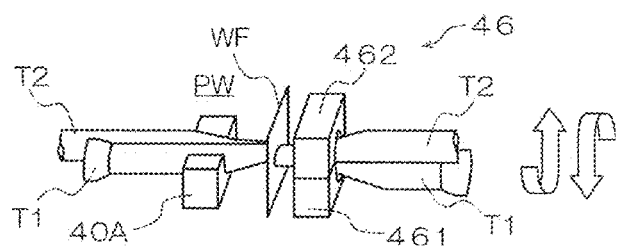
Figure 19D:
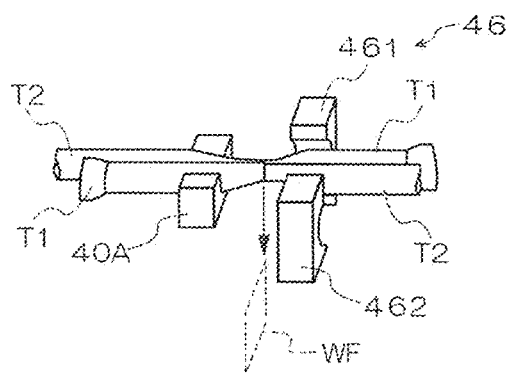

After the fusing work is performed as illustrated in FIG. 19C, in the tube joining device 1, the movable clamp unit 72 is rotated to rotate the end of the first tube T1 on the other side and the end of the second tube T2 on the other side, thereby replacing positions of the both ends. Then, as illustrated in FIG. 19D, the replaced ends of the tubes T1 and 12 are pressed against each other, and are pressure-joined.

Figure 20A:
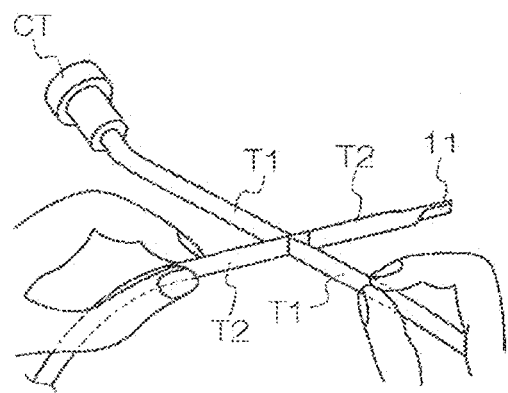
Figure 20B:
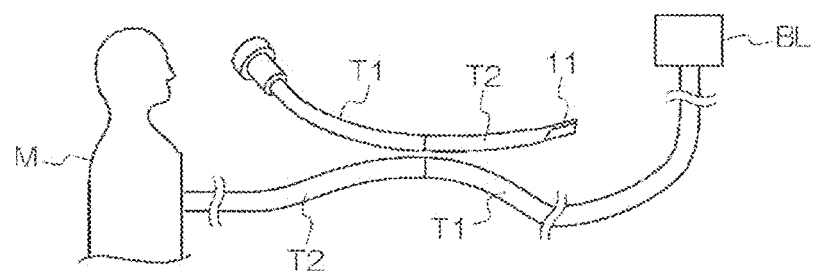

After the joining is completed, the housing 2 is opened as illustrated in FIG. 1 to expose the inside of the housing 2 to the outside. According to this, the user can detach the tubes T1 and T2 from the device. When the joining is completed, the tubes T1 and T2 enter a joined state as illustrated in FIG. 20A. The user detaches the tubes T1 and T2 from the clamp portion 46, and performs work of separating the tubes T1 and T2. When the separation work is performed, as illustrated in FIG. 20B, it is possible to obtain a tube in which the end of the first tube T1 on the one side is joined to the end of the second tube T2 on the other side, and a tube in which the end of the first tube T1 on the other side is joined to the end of the second tube T2 on the one side.

After using the tube joining device 1, the housing 2 is set to a closed state. When using the tube joining device 1 again, if the tube joining device 1 is powered on, the movable clamp unit 72 automatically rotates to perform a reset operation of returning the position of the tube holding section 4, the clamp portion 46, and the tube holding portion 6 to the original position. According to this, the tube holding section 4 is disposed at an initiation position (initial position) of the fusing-joining work as illustrated in FIG. 1. Accordingly, it is possible to perform the fusing-joining work by operating the tube joining device 1 in the same procedure as the above-described procedure.

As described above, the tube joining device 1 according to this embodiment is a tube joining device that fuses an end of the first tube T1 and an end of the second tube T2 by the wafer WF (plate-shaped cutting member) that is heated, and replaces a fused end of the first tube T1 and a fused end of the second tube T2 and joins the fused ends in an aseptic condition and sterile condition. The tube joining device 1 includes the first tube holding portion 41 that can hold the first tube T1, the second tube holding portion 42 that is disposed adjacent to the first tube holding portion 41 and can hold the second tube T2 at a position that is parallel to the first tube T1, and the housing 2 that is provided with the cover member 20 that is closed to cover the fusing-joining sites C of the first tube T1 and the second tube T2. The cover member 20 is slidable in a direction in which the first tube T1 and the second tube T2 are disposed in parallel.

According to the tube joining device 1 configured as described above, a user can dispose the tubes T1 and T2 in parallel by setting the tubes T1 and T2 individually in the first and second tube holding portions 41 and 42. In addition, the user can cause the tubes T1 and T2 to be pressed against each other to come into close contact with each other by operating the cover member 20 that is provided in the tube joining device 1, and thus it is possible to perform setting work of the tubes in a simple manner. As described above, when using the tube joining device 1, it is not necessary for the user to manually perform work of superimposing the tubes T1 and 12, and thus it is possible to prevent a work error such as setting of the tubes in a distorted state from occurring. In addition, since the cover member 20 is slidable along a direction in which the first tube T1 and the second tube T2 are disposed in parallel, it is possible to visually confirm a setting position of the tubes T1 and T2 up to a time immediately before the cover member 20 is closed. Accordingly, it is possible to prevent a joining failure caused by a tube setting error from occurring in advance.

In addition, the cover member 20 includes the first pressing member 21 and the second pressing member 22 which are capable of relatively approaching each other or being relatively separated from each other along the sliding directions X1 and X2, and maintain the first tube T1 and the second tube T2 in a pressed state in accordance with the approaching movement. The first tube holding portion 41 and the second tube holding portion 42 are disposed between the first pressing member 21 and the second pressing member 22. The housing 2 includes the first link mechanism 100 that causes the first tube holding portion 41 and the second tube holding portion 42 to approach the first pressing member 21 or to be separated therefrom in synchronization with the approach or separation of the first pressing member 21 and the second pressing member 22. It is possible to provide a tube joining device which can bring the tubes T1 and T2 into close contact with each other through a simple operation of causing the first pressing member 21 and the second pressing member 22 to approach each other and of which convenience is further improved. In addition, the movement of the first and second tube holding portions 41 and 42 synchronizes with the movement of the first and second pressing members 21 and 22 due to the first link mechanism 100, and thus it is possible to perform work of pressing the first tube T1 and the second tube T2 to come into close contact with each other while holding the tubes T1 and T2 by the first and second tube holding portions 41 and 42.

In addition, when the first pressing member 21 and the second pressing member 22 relatively move, the first link mechanism 100 maintains the position of the first tube holding portion 41 and the second tube holding portion 42 at substantially the center PC between the first pressing member 21 and the second pressing member 22, and thus it is possible to uniformly compress the first tube T1 and the second tube T2 from the sliding directions X1 and X2 of the cover member 20.

In addition, the first tube holding portion 41 and the second tube holding portion 42 include the joining site holding portion 43 that holds the fusing-joining site C of each of the first tube T1 and the second tube T2. The housing 2 includes the second link mechanism 200 that retracts the joining site holding portion 43 from a space between the first pressing member 21 and the second pressing member 22 in synchronization with the approach or separation of the first pressing member 21 and the second pressing member 22. According to this, it is possible to reliably maintain a state in which fusing-joining sites C of the tubes T1 and T2 are disposed in parallel until the first tube T1 and the second tube T2 are pressed to come into close contact with each other.

In addition, the first tube holding portion 41 and the second tube holding portion 42 include the partition portion 44 that is disposed between the fusing-joining site C1 of the first tube T1 and the fusing-joining site C2 of the second tube T2 side. The housing 2 includes the third link mechanism 300 that retracts the partition portion 44 from a space between the first pressing member 21 and the second pressing member 22 in synchronization with the approach or separation of the first pressing member 21 and the second pressing member 22. According to this, the tubes T1 and the T2 are partitioned by the partition portion 44, and thus it is possible to more reliably prevent occurrence of a work error such as setting in a state in which the fusing-joining sites C of the tubes T1 and T2 are distorted. In addition, since it is possible to retract the partition portion 44 from the space between the fusing-joining sites C of the tubes T1 and T2 by the third link mechanism. 300 before the fusing work and the joining work of the tubes T1 and T2, it is possible to smoothly perform the fusing work and the joining work.

In addition, the housing 2 includes the operation panel unit 7 including switches, and the operation panel unit 7 is disposed on the front surface portion 2A of the housing 2 which is located in the directions Y1 and Y2 which intersect the sliding directions X1 and X2 of the cover member 20. According to this, when a user sets the tubes T1 and T2, the operation panel unit 7 is located in front of the user, and thus an operation becomes easy. As a result, it is possible to provide the tube joining device 1 of which convenience is further improved.

Hereinbefore, description has been given of the tube joining device according to the invention with reference to the embodiment, but the invention is not limited to the configuration described in the embodiment, and can be appropriately modified on the basis of the appended claims.

For example, the configuration of the housing or the respective portions of the tube joining device can be modified in correspondence with a use and a purpose of the device, design circumstances and the like, and thus there is no limitation to the configuration illustrated in the drawing. For example, the pressing portions may be configured to cause at least one tube to approach the other tube to be pressed against each other, and are not limited to the configuration in which both the tubes are caused to approach each other as described in this embodiment.

In addition, the tubes which become a joining target may be tubes of which positions of ends after being fused are replaced with each other and are subjected to pressure-joining, and there is no limitation to the tubes used in the peritoneal dialysis.

In addition, description has been given of an example in which the first tube holding portion holds the first tube, and the second tube holding portion holds the second tube, but there is no limitation thereto. The first tube holding portion can hold the second tube, and the second tube holding portion can hold the first tube.

Priority is claimed on Japanese Patent Application No. 2017-059208, filed Mar. 24, 2017, the content of which is incorporated herein by reference.

REFERENCE SIGNS LIST

1 TUBE JOINING DEVICE
2 HOUSING
20 COVER MEMBER
21 FIRST PRESSING MEMBER
22 SECOND PRESSING MEMBER
23 GAP
3 BASE
4 TUBE HOLDING SECTION
41 FIRST TUBE HOLDING PORTION
42 SECOND TUBE HOLDING PORTION
43 JOINING SITE HOLDING PORTION
44 PARTITION PORTION
45 SUPPORT MEMBER
45A SLIDING GROOVE
7 OPERATION PANEL UNIT
100 FIRST LINK MECHANISM
110 FIRST LINK MEMBER
120 SECOND LINK MEMBER
131 FIRST SUPPORT PORTION
132 SECOND SUPPORT PORTION
133 THIRD SUPPORT PORTION
140 HOLDING MEMBER
150 SECOND HOLDING MEMBER
200 SECOND LINK MECHANISM
210 FIRST LINK MEMBER
300 THIRD LINK MECHANISM
310 FIRST LINK MEMBER
320 SECOND LINK MEMBER
330 THIRD LINK MEMBER
500 CONTROL UNIT
C FUSING-JOINING SITE
C1 FUSING-JOINING SITE OF FIRST TUBE
C2 FUSING-JOINING SITE OF SECOND TUBE
PC SUBSTANTIALLY CENTER BETWEEN FIRST PRESSING MEMBER AND SECOND PRESSING MEMBER
T1 FIRST TUBE
T2 SECOND TUBE
WF WAFER

The invention claimed is:

1. A tube joining device that fuses a first tube and a second tube using a plate-shaped cutting member that is heated, and superimposes a fusible end of the first tube on a fusible end of the second tube and joins the fusible ends in an aseptic condition, the tube joining device comprising:
 a plate-shaped cutting member;
 means for heating said cutting member;
 a first tube holding portion that is capable of holding a first tube;
 a second tube holding portion that is disposed adjacent to the first tube holding portion, and is capable of holding a second tube parallel to the first tube in a tube extension direction; and
 a housing that is provided with a cover member that is closed to cover a fusing-joining site of the first tube and a fusion-joining site of the second tube,
 wherein the cover member is slidable along a sliding direction perpendicular to the tube extension direction and further includes a first pressing member and a second pressing member which are configured to approach each other or to separate from each other along the sliding direction, and to maintain the first tube and the second tube in a pressed state,
 the first tube holding portion and the second tube holding portion are disposed between the first pressing member and the second pressing member, and
 the housing includes a first link mechanism that causes the first tube holding portion and the second tube holding portion to approach the first pressing member or to separate therefrom in synchronization with the approach or separation of the first pressing member and the second pressing member.

2. The tube joining device according to claim 1, wherein when the first pressing member and the second pressing member move, the first link mechanism maintains the first tube holding portion and the second tube holding portion at a center position between the first pressing member and the second pressing member.

3. The tube joining device according to claim 2,
wherein the first tube holding portion and the second tube holding portion include a partition portion that is disposed between the fusing-joining site of the first tube and the fusing-joining site of the second tube, and
the housing includes a retraction link mechanism that retracts the partition portion from a space between the first pressing member and the second pressing member in synchronization with the approach of the first pressing member and the second pressing member.

4. The tube joining device according to claim 3,
wherein the housing includes an operation panel unit including switches, and
the operation panel unit is disposed on a front surface portion of the housing which is located in a direction that intersects the sliding direction of the cover member.

5. The tube joining device according to claim 2,
wherein the first tube holding portion and the second tube holding portion include a joining site holding portion that holds the fusing-joining site of the first tube and the fusion-joining site of the second tube, and
the housing includes a second link mechanism that retracts the joining site holding portion from a space between the first pressing member and the second pressing member in synchronization with the approach of the first pressing member and the second pressing member.

6. The tube joining device according to claim 5,
wherein the housing includes an operation panel unit including switches, and
the operation panel unit is disposed on a front surface portion of the housing which is located in a direction that intersects the sliding direction of the cover member.

7. The tube joining device according to claim 5,
wherein the first tube holding portion and the second tube holding portion include a partition portion that is disposed between the fusing-joining site of the first tube and the fusing-joining site of the second tube side, and
the housing includes a retraction link mechanism that retracts the partition portion from the space between the first pressing member and the second pressing member in synchronization with the approach of the first pressing member and the second pressing member.

8. The tube joining device according to claim 7,
wherein the housing includes an operation panel unit including switches, and
the operation panel unit is disposed on a front surface portion of the housing which is located in a direction that intersects the sliding direction of the cover member.

9. The tube joining device according to claim 1,
wherein the housing includes an operation panel unit including switches, and
the operation panel unit is disposed on a front surface portion of the housing which is located in a direction that intersects the sliding direction of the cover member.

10. The tube joining device according to claim 1,
wherein the first tube holding portion and the second tube holding portion include a joining site holding portion that holds the fusing-joining site of the first tube and the fusion-joining site of the second tube, and
the housing includes a second link mechanism that retracts the joining site holding portion from a space between the first pressing member and the second pressing member in synchronization with the approach of the first pressing member and the second pressing member.

11. The tube joining device according to claim 10,
wherein the first tube holding portion and the second tube holding portion include a partition portion that is disposed between the fusing-joining site of the first tube and the fusing-joining site of the second tube, and
the housing includes a retraction link mechanism that retracts the partition portion from the space between the first pressing member and the second pressing member in synchronization with the approach of the first pressing member and the second pressing member.

12. The tube joining device according to claim 11,
wherein the housing includes an operation panel unit including switches, and
the operation panel unit is disposed on a front surface portion of the housing which is located in a direction that intersects the sliding direction of the cover member.

13. The tube joining device according to claim 1,
wherein the first tube holding portion and the second tube holding portion include a partition portion that is disposed between the fusing-joining site of the first tube and the fusing-joining site of the second tube, and
the housing includes a retraction link mechanism that retracts the partition portion from a space between the first pressing member and the second pressing member in synchronization with the approach or separation of the first pressing member and the second pressing member.

14. The tube joining device according to claim 13,
wherein the housing includes an operation panel unit including switches, and
the operation panel unit is disposed on a front surface portion of the housing which is located in a direction that intersects the sliding direction of the cover member.

* * * * *